US009989497B2

(12) United States Patent
Walker et al.

(10) Patent No.: US 9,989,497 B2
(45) Date of Patent: Jun. 5, 2018

(54) FRONT END CIRCUITRY WITH ANALOG SAMPLING AND DECODING FOR ULTRASOUND IMAGING SYSTEMS AND METHODS OF USE

(75) Inventors: William F. Walker, Earlysville, VA (US); Michael I. Fuller, Williamsburg, VA (US); Karthik Ranganathan, Cambridge, MA (US); John A. Hossack, Charlottesville, VA (US); Travis N. Blalock, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 1186 days.

(21) Appl. No.: 12/543,452

(22) Filed: Aug. 18, 2009

(65) Prior Publication Data
US 2010/0063399 A1     Mar. 11, 2010

Related U.S. Application Data

(60) Provisional application No. 61/089,686, filed on Aug. 18, 2008.

(51) Int. Cl.
*A61B 8/00* (2006.01)
*G01N 29/36* (2006.01)
(Continued)

(52) U.S. Cl.
CPC ...... *G01N 29/0654* (2013.01); *G01S 7/52026* (2013.01); *G01S 7/52046* (2013.01);
(Continued)

(58) Field of Classification Search
CPC ......... A61B 8/00; A61B 8/44; G01N 29/0654
(Continued)

(56) References Cited

U.S. PATENT DOCUMENTS 5,469,851 A * 11/1995 Lipschutz ............... 600/447
6,013,032 A *  1/2000 Savord .................. 600/443
(Continued)

FOREIGN PATENT DOCUMENTS

WO    WO-2010021709 A1    2/2010

OTHER PUBLICATIONS

Fuller et al. A Portable, Low-Cost, Highly Integrated, 3D Medical Ultrasound System, 2003 IEEE Ultrasonics Symposium-38.*
(Continued)

*Primary Examiner* — Serkan Akar
(74) *Attorney, Agent, or Firm* — Schwegman Lundberg & Woessner, P.A.

(57) ABSTRACT

Pulse-echo imaging systems and methods are provided, including a transmit code sequencer and a pulse generation circuit, The transmit code sequencer is configured to input a transmit code sequence to the pulse generation circuit. A transducer is configured to receive electrical signals provided as pulses using coded excitation according to the transmit code sequence, and to transduce the electrical signals to pulses of energy other than electrical signals. The transducer is further configured to receive echoes of the pulses of energy other than electrical signals and convert the echoes to received electrical signals generate using coded excitation. A receive circuit is configured to receive the received electrical signals generate using coded excitation, perform analog sampling of the received electrical signals generate using coded excitation, and provide a weighted, summed digital signal by processing the analog samples. At least one example of a pulse imaging system described is configured for ultrasonic pulse-echoes. At least one example of a pulse imaging system described is a medical diagnostic imaging system.

43 Claims, 18 Drawing Sheets

(51) Int. Cl.
  *G06K 9/00* (2006.01)
  *G01N 29/06* (2006.01)
  *G01S 7/52* (2006.01)
  *G01S 15/89* (2006.01)

(52) U.S. Cl.
  CPC ...... *G01S 7/52079* (2013.01); *G01S 15/8959* (2013.01); *A61B 8/00* (2013.01); *A61B 8/4483* (2013.01); *G01N 2291/02475* (2013.01)

(58) Field of Classification Search
  USPC .................... 600/443, 437, 447, 454
  See application file for complete search history.

(56) References Cited

U.S. PATENT DOCUMENTS

| | | | |
|---|---|---|---|
| 6,042,545 A * | 3/2000 | Hossack et al. | 600/443 |
| 6,155,980 A | 12/2000 | Chiao et al. | |
| 6,179,780 B1 * | 1/2001 | Hossack et al. | 600/437 |
| 6,210,332 B1 * | 4/2001 | Chiao et al. | 600/443 |
| 6,213,947 B1 | 4/2001 | Phillips | |
| 6,517,488 B1 * | 2/2003 | Hossack | 600/454 |
| 6,760,486 B1 | 7/2004 | Chiao et al. | |
| 6,790,182 B2 | 9/2004 | Eck et al. | |
| 6,796,944 B2 | 9/2004 | Hall | |
| 6,824,518 B2 | 11/2004 | Von Behren et al. | |
| 6,842,401 B2 | 1/2005 | Chiang et al. | |
| 6,940,450 B2 | 9/2005 | Blunt et al. | |
| 7,037,265 B2 | 5/2006 | Hao et al. | |
| 7,094,204 B2 | 8/2006 | Banjanin et al. | |
| 7,106,250 B2 | 9/2006 | Blunt et al. | |
| 7,338,448 B2 | 3/2008 | Hao et al. | |
| 2005/0054925 A1 * | 3/2005 | Hao et al. | 600/443 |
| 2005/0154303 A1 | 7/2005 | Blalock et al. | |
| 2006/0052697 A1 | 3/2006 | Hossack et al. | |
| 2007/0016022 A1 | 1/2007 | Blalock et al. | |
| 2007/0016044 A1 | 1/2007 | Blalock et al. | |

OTHER PUBLICATIONS

Band-pass Filters _ Filters—Electronics Textbook.*
Wang et al_2003_Coded EXcitation with Spectrum Inversion for Ultrasound Array Imaging.*
"European Application Serial No. 09808508.7, Extended Search Report dated Jan. 19, 2012", 5 pgs.
"European Application Serial No. 09808508.7, Response filed Jul. 30, 2012 to Extended EP Search Report dated Jan. 19, 2012", 11 pgs.

* cited by examiner

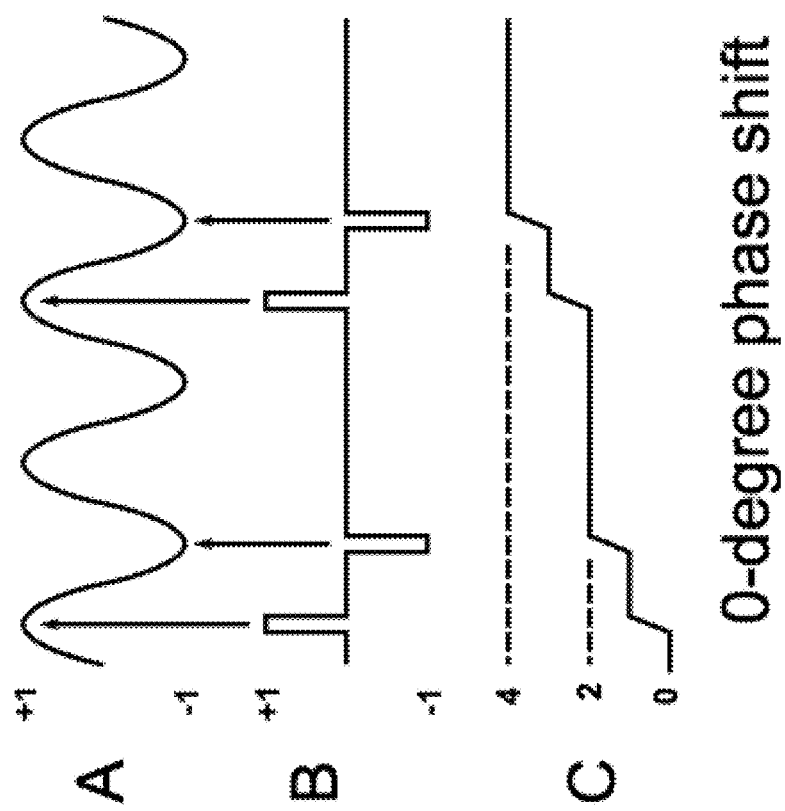

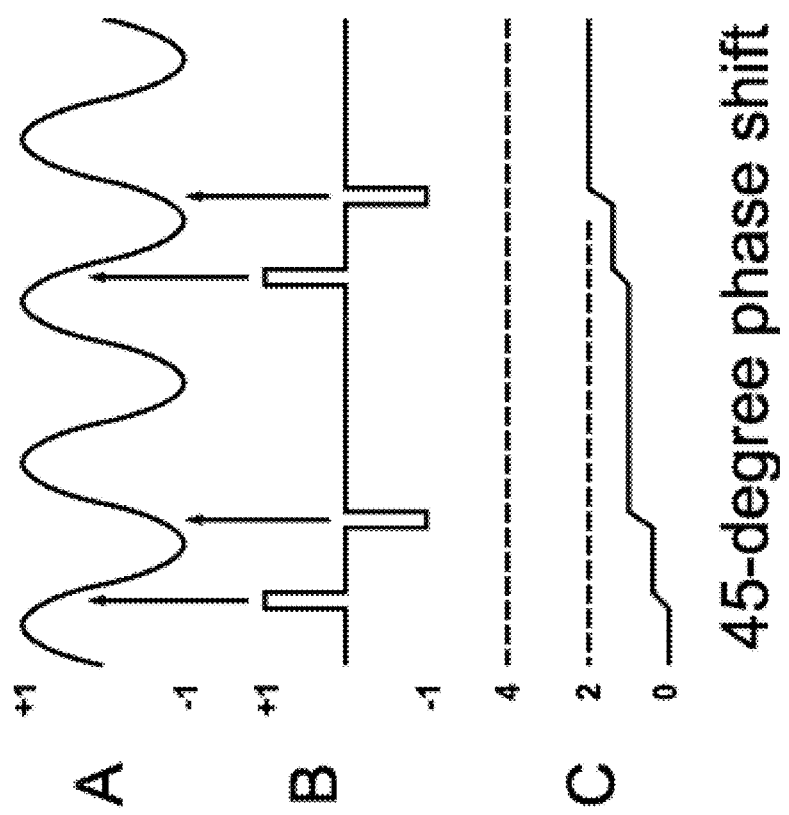

FRONT END CIRCUITRY WITH ANALOG SAMPLING AND DECODING FOR ULTRASOUND IMAGING SYSTEMS AND METHODS OF USE

CROSS-REFERENCE

This application claims the benefit of U.S. Provisional Application No. 61/089,686, filed Aug. 18, 2008, which application is hereby incorporated herein, in its entirety, by reference thereto.

The following patents and patent application publications are hereby incorporated herein, in their entireties, by reference thereto: Chiao et al., U.S. Pat. No. 6,155,980; Chiao et al., U.S. Pat. No. 6,210,332; Phillips, U.S. Pat. No. 6,213,947; Hossack et al., U.S. Patent Application Publication No. 2006/0052697A1; Walker et al., U.S. Patent Application Publication No. 2005/0154303A1; Blalock et al., U.S. Patent Application Publication No. 2007/0016044; and Blalock et al., U.S. Patent Application Publication No. 2007/0016022.

GOVERNMENT RIGHTS

This invention was made with government support under federal grant nos. 5R42RR020834 and 1 R43 HL084804-01 awarded by the National Institutes of Health/NCRR and the National Institutes of Health/NHLBI, respectively. The United States Government has certain rights in this invention.

BACKGROUND OF THE INVENTION

State-of-the-art ultrasound imaging systems transmit and receive ultrasound using a transducer that comprises multiple elements forming a transducer array. Imaging is accomplished by transmitting ultrasound pulses and focusing the received echoes to form a two or three-dimensional image.

The transducer array, which typically comprises multiple elements, converts an electrical signal into ultrasound and vice versa. The elements are arranged to form either a one-dimensional (1D) or, increasingly, a two-dimensional (2D) array, and are driven by excitation pulses generated by high-voltage (typically 100 V or greater) transmit circuits. Prior to amplification by high-voltage pulsers, the transmit waveforms are delayed by a transmit beamformer to focus the resulting ultrasound beam at a point of interest. Typically, each element of the transducer array is also amplitude weighted to shape the ultrasound beam by a process known as apodization. The transmit beamformer controls focusing and apodization, along with transmit pulse shape in advanced systems.

Ultrasound waves emitted by the transducer array impact objects in the field that the beam is focused to. Reflected ultrasound waves (echoes) are reflected off of the objects impacted by the emitted ultrasound waves. Echoes that are reflected back to the transducer array are transduced from ultrasonic waves to electrical signals (received signals). The received signals are amplified, filtered, and then, in almost all cases, digitized by analog to digital converters (A/Ds). These digitized signals are then focused and apodized by the receive beamformer, followed by image processing and scan conversion for display on a monitor. Some systems have Doppler circuits to estimate blood flow, whose output is either fed to speakers or displayed on the monitor.

In addition to the provision of circuit blocks to accomplish the above-mentioned functions, ultrasound systems also contain protection circuits in the receive data path. The transducer array elements are inefficient and, as such, require a high-voltage input to generate the ultrasound waves that are emitted by the transducer array. Likewise, due to the inefficiency of the transducer array elements, transduction of the received echoes results in low-voltage received signals. As ultrasound is generated by driving transducers with high-voltage pulses, the low-voltage receive circuits must be isolated from these transmit pulses to prevent permanent damage to the receive circuits. These protection circuits can impose major constraints on ultrasound systems. Size becomes a factor as ultrasound systems shrink into ever-smaller form factors and the number of receive channels (paths) increases. Interconnect complexity, which relates to forming an electrical connection between each transducer element and its receive channel, is complicated by the need to place protection circuit components within this signal path. This interconnect problem is particularly challenging for 2D array-based systems where element and channel counts increase exponentially relative to that of 1D array systems. Component costs can also be significant, as necessary high-voltage components are costly and large. Moreover, active protection circuits (such as high-voltage switches) need power to operate, whereas passive protection circuits (such as diode limiters/expanders) shunt a significant portion of the transmit energy to ground away from the transducer, leading to an inefficient system.

The weak amplitude of the received signal is another major problem, requiring amplification prior to digitization. However, the underlying noise is amplified as well, and front-end components such as the transmit protection circuitry and preamplifier inject additional noise into the signal. This leads to a signal-to-noise ratio (SNR) that can be critically low. As ultrasound waves are attenuated by the medium in which they propagate, low SNR limits the maximum imaging depth.

One strategy to overcome this problem is to reduce the frequency of the transmitted ultrasound pulse, as lower frequencies are attenuated less and return stronger signals to the transducer. However, a lower imaging frequency has the undesirable effect of lowering image resolution.

Another strategy is to simply increase the magnitude of the electrical excitation. A stronger ultrasound wave is then transmitted into the structure being imaged and, consequently, a stronger signal is reflected and received. There are also problems with this approach however as in diagnostic ultrasound imaging, there are strict limitations on the strength of the ultrasound signal that is transmitted into the body. Most of the transmitted ultrasound energy is converted into heat in tissue and there is therefore a danger of overheating tissue. Moreover, too high a magnitude might result in cavitation in tissue, i.e., the production and destruction of microscopic gas bubbles. To eliminate these dangers, the Food and Drug Administration (FDA) places restrictions on the peak negative pressure induced by ultrasound waves in tissue. As peak pressure is directly governed by the magnitude of the transmitted ultrasound signal, ultrasound systems regulate the magnitude of the electrical excitation that drives the transducer.

Coded excitation is a third method that overcomes these challenges to improve the SNR of the received signal. Using coded excitation, the base excitation pulse is convolved with a code that lengthens the transmitted pulse while complying with FDA regulations that govern peak pressure. The resulting longer ultrasound pulse contains more energy, which translates into stronger echoes from targets and a higher SNR in the received signal. The received signal is then "compressed" to eliminate the lengthening effect of the code, while still preserving the extra energy. There are several strategies to compress the received signal: examples include convolution with a matched filter that corresponds to the code or with a custom "mismatched filter" to shape the compressed pulse into one having preferred characteristics. U.S. Pat. No. 6,155,980 entitled "Ultrasonic imaging system with beamforming using unipolar or bipolar coded excitation" assigned to the General Electric Company describes a method for implementing bipolar coded excitation in medical ultrasound systems that have unipolar pulsers and suffer code degradation due to nonlinear propagation. U.S. Pat. No. 6,155,980 is hereby incorporated herein, in its entirety, by reference thereto. A major motivation of the technique was improving SNR. U.S. Pat. No. 6,210,332 entitled, "Method and apparatus for flow imaging using coded excitation" and assigned to the General Electric Company describes the application of coded excitation to improve the SNR of signals used in blood flow estimation. U.S. Pat. No. 6,210,332 is hereby incorporated herein, in its entirety, by reference thereto.

Coded excitation is also used to enhance the speed of ultrasound imaging and increase frame rate. In this scenario, multiple codes are transmitted at the same time or with a short element-to-element delay. This enables simultaneous imaging in different directions and therefore a reduction in imaging time. U.S. Pat. No. 6,213,947 entitled "Medical diagnostic ultrasonic imaging system using coded transmit pulses" assigned to the Acuson Corporation describes one use of coded excitation to increase frame rates. U.S. Pat. No. 6,213,947 is hereby incorporated herein, in its entirety, by reference thereto.

Prior methods for implementing coded excitation, including those cited above, require more hardware resources than are available in imaging systems limited by power, cost and/or area constraints. An example of such a system is the low-cost, hand-held, C-scan ultrasound device described in U.S. patent applications 2006/0052697A1, 2005/0154303A1, 2007/0016044, and 2007/0016022, each of which is hereby incorporated herein, in its entirety, by reference thereto. The C-scan ultrasound device described utilizes a 2D transducer array in conjunction with one unique receive channel for every transducer element. All receive channels acquire the data for a single C-scan image, in parallel. The C-scan images can be formed with as few as four samples (U.S. patent application 2007/0016022), so the integrated circuitry can be fully implemented within a very small area on silicon. Significant power savings are achieved by switching off the receive electronics between relatively sporadic transmit/receive events, which can amount to digitization rates and power duty cycles as slow as the frame rate (~30 Hz). The small channel area, low digitization rates, and efficient power consumption are directly related to the number of samples that must be acquired and digitized to form each image. Since coded excitation increases the length of the acoustic pulse and since prior methods for implementing coded excitation perform the decoding in the digital domain, the number of samples that must be acquired and digitized to form a C-scan image increases as a multiple of the code length. Such an implementation choice is therefore incompatible with the hardware constraints of the example C-scan ultrasound system and for any system having similar constraints.

There is a continuing need for improving the SNR characteristics of ultrasound systems as the systems become smaller and more complex. The present invention provides solutions for such improvements.

SUMMARY OF THE INVENTION

The present invention provides pulse echo imaging systems and methods for processing received signals including analog sampling to alleviate speed requirements of an analog-to-digital converter used.

A pulse-echo imaging system is provided that includes: a transmit code sequencer and a pulse generation circuit, the transmit code sequencer configured to input a transmit code sequence to the pulse generation circuit; a transducer configured to receive electrical signals provided as pulses using coded excitation according to the transmit code sequence, and to transduce the electrical signals to pulses of energy other than electrical signals; the transducer being further configured to receive echoes of the pulses of energy other than electrical signals and convert the echoes to received electrical signals generate using coded excitation; and a receive circuit configured to receive the received electrical signals generate using coded excitation; perform analog sampling of the received electrical signals generate using coded excitation; and to provide a weighted, summed digital signal by processing the analog samples.

In at least one embodiment, the receive circuit weights the analog samples, sums the weighted analog samples and converts then converts a resulting summed, weighted analog signal to a summed, weighted digital signal.

In at least one embodiment, the receive circuit weights the analog samples, converts resulting weighted, analog samples to weighted digital samples, and then sums the weighted digital samples.

In at least one embodiment, the receive circuit converts the analog samples to digital samples, weights the digital samples, and sums the weighted digital samples.

In at least one embodiment, the receive circuit comprises an analog decoder and an analog-to-digital converter, wherein the analog decoder decodes the received electrical signal using coded excitation to provide decoded analog samples and the analog-to-digital converter converts the decoded analog samples to decoded digital samples.

In at least one embodiment, the receive circuit comprises a mixed signal decoder, the receive circuit comprising at least one analog sample and hold circuit and the mixed signal decoder comprises an analog-to-digital converter and a digital-to-analog converter, wherein samples from the at least one sample and hold circuit are received by the analog-to-digital converter, the analog-to-digital converter converts the analog samples to digital samples, and weight of the digital samples are adjusted by scaling of a transfer characteristic of the analog-to-digital converter by input received from the digital-to-analog converter.

In at least one embodiment, the input received from the digital-to-analog converter includes both gain and offset information and wherein the digital samples are corrected for offset and scaled for gain, after which the offset-corrected, gain-scaled digital signals are summed.

In at least one embodiment, the analog decoder comprises a two-level filter.

In at least one embodiment, the analog decoder comprises a switch and a summing device; wherein the received electrical signals generate using coded excitation are directed down two circuit paths of the two-level filter, wherein scaled samples are produced by one of the two circuit paths multiplying the signals by +1 and the other of the two circuit paths multiplying the signals by −1, and, depending upon whether a resulting signal coefficient is +1 or the switch selects one of the circuit paths and passes the scaled sample to the summing device; wherein the summing device sums the scaled samples received to yield a decoded sample.

In at least one embodiment, the receive circuit comprises: a single-ended circuit implementation having two parallel branches, each containing an analog coefficient multiplier; one of the branches comprising an inverting unity gain amplifier and the other of the branches comprising a non-inverting unity gain amplifier; a switch or transmission gate configured to select one of the branches based upon a filter coefficient assigned by the amplifiers; the selected branch feeding into a single-ended sampling switched-capacitor integrator with reset capability that samples a continuous signal during one phase to provide a sampled signal and adds the sampled signal to previous sampled signals during a subsequent phase.

In at least one embodiment, the receive circuit comprises a differential circuit. The differential circuit includes: a switching circuit that implements positive and negative coefficients by interchanging positive and negative terminals of differential branches of the differential circuit; and a differential sampling, switched capacitor integrator with reset capability configured to sample a continuous signal during one phase to provide a sampled signal, and, in a second phase, to add the sampled signal to previous sampled signals.

In at least one embodiment, the receive circuit comprises more than two parallel circuit paths, a switching device and a summing device; wherein the received electrical signals generate using coded excitation are directed down the more that two circuit paths, wherein scaled samples are produced by the more than two circuit paths, each containing an analog multiplier having a gain set to provide multiple arbitrary filter coefficients where each branch assigns a different filter coefficient, and, depending upon the resulting signal coefficient, the switch device selects one of the circuit paths having a predefined one of the filter coefficients and passes the scaled sample from the selected circuit path to the summing device; wherein the summing device sums the scaled samples received to yield a decoded sample.

In at least one embodiment, the receive circuit comprises: a single-ended circuit implementation having two parallel branches, each containing an adjustable sampling capacitor; each adjustable sampling capacitor being adjustable for multiple different coefficient values configured for decoding coded excitation signals using different codes.

In at least one embodiment, the differential includes: a switching circuit capable of implementing more than two different filter coefficients by interchanging positive and negative terminals of differential branches of the differential circuit and by providing each differential branch with an adjustable sampling capacitor that is adjustable for multiple different coefficient values; and a differential sampling, switched capacitor integrator with reset capability configured to sample a continuous signal during one phase to provide a sampled signal, and, in a second phase, to add the sampled signal to previous sampled signals.

In at least one embodiment, the receive circuit comprises: a plurality of sample and hold units, each provided for sampling and holding one sample of the received electrical signals over one code length; and a switched-capacitor integrator configured to commence integration and integrate the samples after all samples from an entire received pulse have been acquired by the sample and hold units.

In at least one embodiment, the receive circuit includes an analog memory bank provided for holding each sample of the received electrical signals over one code length; and a switched-capacitor integrator configured to commence integration and integrate the samples after all samples from an entire received pulse have been held by the analog memory.

In at least one embodiment, a charge storage capacity of each of the sample and hold units is set as a function of a predefined filter coefficient, respectively.

In at least one embodiment, the analog memory comprises a plurality of memory cells each having a charge storage capacity, wherein the charge storage capacity of each of the memory cells is set as a function of a predefined filter coefficient, respectively.

In at least one embodiment, each sample and hold unit comprises an adjustable sampling capacitor, each adjustable sampling capacitor being adjustable for more than two different coefficient values.

In at least one embodiment, the receive circuit includes a plurality of sample and hold units, each provided for sampling and holding one sample of the received electrical signals over one code length; and an operational amplifier configured as a summing operational amplifier, configured to commence integration and integrate the samples after all samples from an entire received pulse have been acquired by the sample and hold units.

In at least one embodiment, the receive circuit includes an analog memory bank provided for holding each sample of the received electrical signals over one code length; and an operational amplifier configured as a summing operational amplifier, configured to commence integration and integrate the samples after all samples from an entire received pulse have been held by the analog memory.

In at least one embodiment, the receive circuit includes a single-ended circuit implementation having two parallel branches, each containing an analog coefficient multiplier; one of the branches comprising an inverting unity gain amplifier and the other of the branches comprising a non-inverting unity gain amplifier; a switch or transmission gate configured to select one of the branches based upon a filter coefficient assigned by the amplifiers; the selected branch feeding into an input of an integrator comprising a transconductance amplifier and an integrating capacitor, wherein the transconductance amplifier converts charge received through the switch or transmission gate into current and the current is inputted to the integrating capacitor.

In at least one embodiment, the receive circuit includes a differential circuit. The differential circuit includes a switching circuit that implements positive and negative coefficients by interchanging positive and negative terminals of differential branches of the differential circuit; and an integrator comprising a transconductance amplifier and an integrating capacitor, wherein the transconductance amplifier converts charge received from the switching circuit into current and the current is inputted to the integrating capacitor.

In at least one embodiment, wherein the summing device includes an integrator comprising a transconductance amplifier and an integrating capacitor.

In at least one embodiment, the receive circuit includes a single-ended circuit implementation having two parallel branches, each containing an analog coefficient multiplier; one of the branches comprising an inverting unity gain amplifier and the other of the branches comprising a non-inverting unity gain amplifier; a switch or transmission gate configured to select one of the branches based upon a filter coefficient assigned by the amplifiers; the selected branch comprising a series switch and a ground switch configured to feed a signal from the selected branch into an input of an integrator comprising a transconductance amplifier and an integrating capacitor, wherein the transconductance amplifier converts charge of the signal into current and the current is inputted to the integrating capacitor.

In at least one embodiment, the receive circuit converts the analog samples to decoded digital samples and the decoded digital samples are used to form C-scan images.

In at least one embodiment, repeated blocks of the receive circuit yield distinct decoded time samples, each decoded time sample being constructed using k received samples, where k is a length of a decoding filter used by the receive circuit, and wherein the k received samples are weighted by filter coefficients of the decoding filter and integrated to yield one of decoded analog sample, wherein the decoded analog samples are digitized to form the decoded digital samples, and wherein the decoded digital samples are apodized and focused to construct C-scan images.

In at least one embodiment, the receive circuit decodes the received electrical signal after apodizing and delaying samples of the received electrical signal.

In at least one embodiment, the receive circuit implements an arbitrary, analog, discrete-time filter.

In at least one embodiment, the pulse generation circuit and the receive circuit are provided on a single integrated circuit.

A diagnostic ultrasound system is provided that includes a transmit code sequencer and a pulse generation circuit, the transmit code sequencer configured to input a transmit code sequence to the pulse generation circuit; a transducer configured to receive electrical signals provided as pulses using coded excitation according to the transmit code sequence, and to transduce the electrical signals to pulses of energy other than electrical signals; the transducer being further configured to receive echoes of the pulses of energy other than electrical signals and convert the echoes to received electrical signals generate using coded excitation; and a receive circuit configured to receive the received electrical signals generate using coded excitation; perform analog sampling of the received electrical signals generate using coded excitation; and to provide a weighted, summed digital signal by processing the analog samples.

In at least one embodiment, the receive circuit comprises an analog decoder and an analog-to-digital converter, wherein the analog decoder decodes the received electrical signal using coded excitation to provide decoded analog samples and the analog-to-digital converter converts the decoded analog samples to decoded digital samples.

In at least one embodiment, the receive circuit comprises a mixed signal decoder, the receive circuit comprising at least one analog sample and hold circuit and the mixed signal decoder comprises an analog-to-digital converter and a digital-to-analog converter, wherein samples from the at least one sample and hold circuit are received by the analog-to-digital converter, the analog-to-digital converter converts the analog samples to digital samples, and weight of the digital samples are adjusted by scaling of a transfer characteristic of the analog-to-digital converter by input received from the digital-to-analog converter.

In at least one embodiment, the input received from the digital-to-analog converter includes both gain and offset information and the digital samples are corrected for offset and scaled for gain, after which the offset-corrected, gain-scaled digital signals are summed.

In at least one embodiment, the diagnostic ultrasound system comprises a medical ultrasonic imaging system.

A method of processing a pulse-echo to generate an image is provided, including: receiving an analog electrical signal converted from a received pulse-echo using coded excitation; analog sampling the electrical signal; and processing the analog samples to produce a weighted, summed, digital signal.

In at least one embodiment, the processing comprises: weighing the analog samples to provide weighted, analog samples; summing the weighted analog samples to provide a summed, weighted, analog signal; and converting the summed, weighted, analog signal to the summed, weighted, digital signal.

In at least one embodiment, the processing comprises: weighting the analog samples to provide weighted, analog samples; converting the weighted, analog samples to weighted digital samples, and summing the weighted digital samples to provide the summed, weighted, digital signal.

In at least one embodiment, the processing comprises: converting the analog samples to digital samples; weighting the digital samples to provide weighted, digital samples; and summing the weighted, digital samples to provide the summed, weighted, digital signal.

In at least one embodiment, the receiving, analog sampling and processing are repeated to provide a plurality of the summed, weighted digital signals; and the method further includes apodizing the summed, weighted digital signals; and focusing the summed, weighted digital signals having been apodized, to construct an image.

In at least one embodiment, the received analog electrical signal is directed down two circuit paths of a two-level filter, wherein scaled samples are produced by one of the two circuit paths multiplying the signals by +1 and the other of the two circuit paths multiplying the signals by −1, and, depending upon whether a resulting signal coefficient is +1 or −1, a switch selects one of the circuit paths and passes the scaled sample as a weighted analog sample to a summing device.

In at least one embodiment, the received analog signal is directed to a differential circuit comprising a switching circuit that implements positive and negative coefficients by interchanging positive and negative terminals of differential branches of the differential circuit; and wherein the processing comprises summing performed by a differential sampling, switched capacitor integrator with reset capability configured to sample a continuous signal during one phase to provide a sampled signal, and, in a second phase, to add the sampled signal to previous sampled signals.

In at least one embodiment, an adjustable sampling capacitor is adjusted in regard to a coefficient value configured for weighting the analog signal.

In at least one embodiment, the weighting is carried out using a switching circuit capable of implementing more than two different filter coefficients by interchanging positive and negative terminals of differential branches of the differential circuit and by providing each differential branch with an adjustable sampling capacitor that is adjustable for multiple different coefficient values.

In at least one embodiment, the weighting is performed using a plurality of sample and hold units, each provided for sampling and holding one sample of the received electrical signal; and the summing is performed by a switched-capacitor integrator configured to commence integration and integrate the samples after all samples from an entire received pulse have been acquired by the sample and hold units.

In at least one embodiment, the weighting is performed using an analog memory bank provided for holding each sample of the received electrical signal over one code length; and wherein the summing is performed using a switched-capacitor integrator configured to commence integration and integrate the samples after all samples from an entire received pulse have been held by the analog memory.

In at least one embodiment, the pulse-echo is an ultrasound pulse-echo.

In at least one embodiment, the image is a C-scan image.

In at least one embodiment, repeated blocks of the received analog signals are weighted and summed to yield distinct weighted time samples, each weighted time sample being constructed using k received samples, where k is a length of a decoding filter used during the weighting, and wherein the k received samples are weighted by filter coefficients of the decoding filter and integrated to yield one of the weighted analog samples, wherein the weighted analog samples are digitized to form the weighted digital samples, and wherein the weighted digital samples are apodized and focused to construct C-scan images.

In at least one embodiment, the weighting comprises taking samples of the electrical signal at selected time intervals to correspond to a delay between reception of the pulse-echo and reception of an aberrant scaled replica of the pulse-echo, so that the pulse-echo and the aberrant scaled replica are scaled and summed by the weighting and summing to effect at least partial cancellation of the aberrant scaled replica.

In at least one embodiment, the processing comprises: weighting and digitizing the samples to form weighted digital samples by converting the analog sampling to digital samples using an analog-to-digital converter and adjusting weights of the digital samples by scaling of a transfer characteristic of the analog-to-digital converter according to an analog reference signal inputted to the analog-to-digital converter; and summing the weighted digital samples to provide a summed decoded digital sample.

In at least one embodiment, the method further includes: repeating the receiving, analog sampling, weighting and digitizing, and summing to provide a plurality of the summed, decoded digital signals: apodizing the summed, decoded digital signals; and focusing the summed, decoded digital signals having been apodized, to construct an image.

These and other features of the invention will become apparent to those persons skilled in the art upon reading the details of the systems and methods as more fully described below.

BRIEF DESCRIPTION OF THE DRAWINGS

FIGS. 5A-5B show timing diagrams for the signals in FIG. 4.

DETAILED DESCRIPTION OF THE INVENTION

Figure 1:
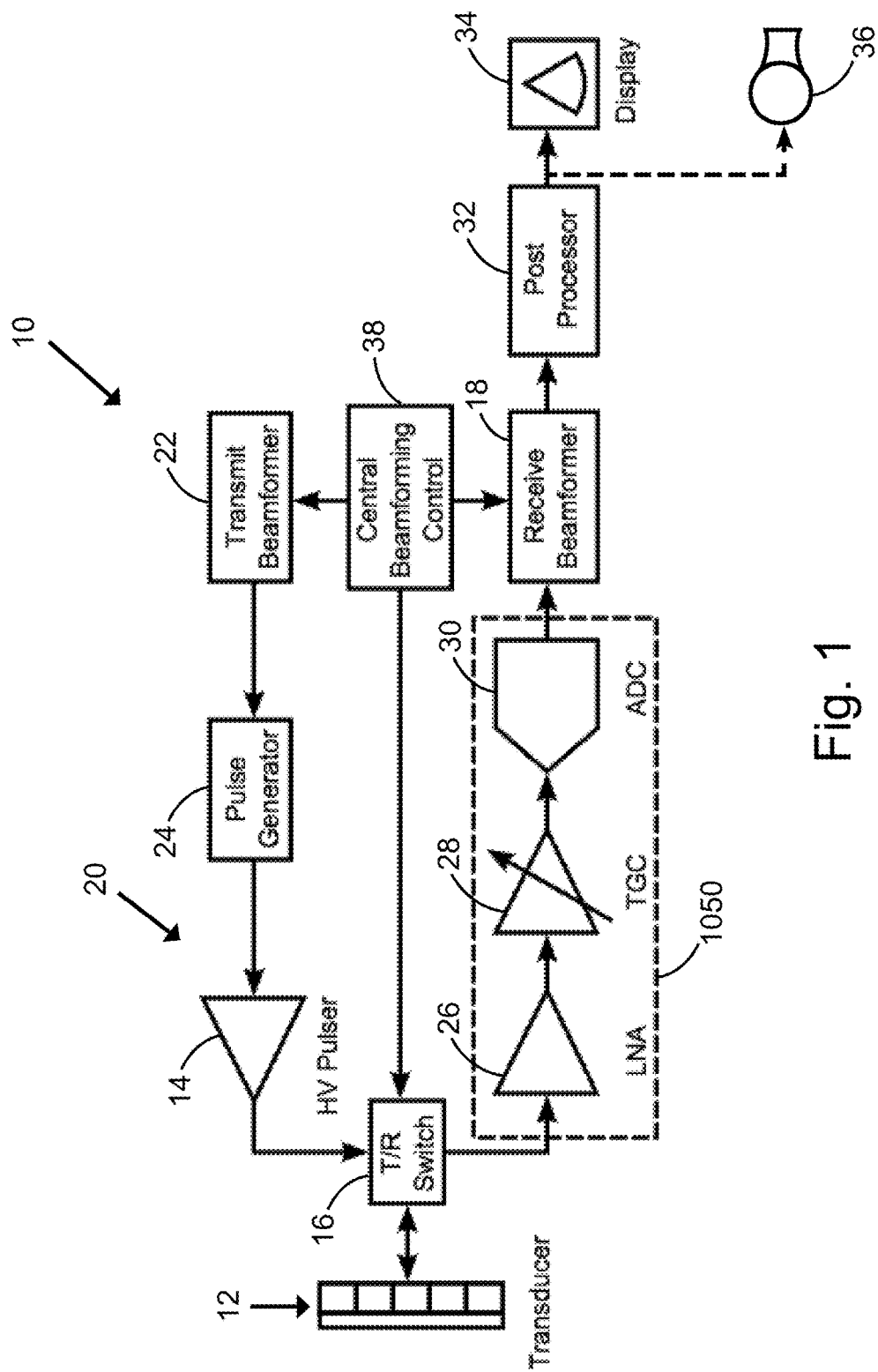
FIG. 1 is a block diagram illustrating main components of an ultrasound imaging system.

Before the present systems, apparatus and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a capacitor" includes a plurality of such capacitors and reference to "the circuit" includes reference to one or more circuits and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The term "code length" refers to the number of arbitrary weights that are convolved with the base excitation pulse to form a new, elongated, encoded pulse. The code length (as well as the amplitude of the weights) is determined in conjunction with the design of the decoding/compression filter to yield desired system performance in terms of signal-to-noise ratio, contrast and resolution.

The "length of a compression filter" refers to the number of arbitrary weights assigned to the decoder. The weights are a sequence of Weights convolved with the encoded received echo signal (pre- or post-beamformed) to yield the decoded signal. The number (and amplitude) of these weights are related, but not necessarily identical, to the length of the encoded sequence. The number of total weights and the amplitude of each weight is designed in conjunction with the code on transmit to yield desired system performance in terms of signal-to-noise ratio, contrast and resolution.

FIG. 1 is a block diagram illustrating main components of an ultrasound imaging system 10. System 10 includes a transducer array 12 that typically comprises multiple transducer elements A transducer element as used herein is not limited to a single-electro-mechanical structure, although that is one embodiment of a transducer. For example, a transducer element may be layered so that one layer handles transmit pulses and another layer received pulses and therefore separate transmit and receive connections are made to such a transducer element. Likewise, a transducer array 12 may contain an array of transducer elements that are each a single electro-mechanical structure, or a transducer array many contain an array of transducer elements that are layered as described. Transducer array 12 converts an electrical signal received from the high-voltage pulser 14 into ultrasound that is emitted from the transducer 12. Echoes of ultrasound energy that are received by the transducer array 12 are converted to electrical signals and routed (through transmit/receive switch 16) to the receive beamformer 18. The elements of transducer 12 are arranged to form either a 1D or a 2D array, and are driven by excitation pulses generated by high-voltage (typically 100 V or greater) transmit circuits 20. Prior to amplification by high-voltage pulsers 14, the transmit waveforms are delayed by the transmit beamformer 22 to focus the resulting ultrasound beam at the point of interest. Typically, each element is also amplitude weighted to shape the ultrasound beam, a process known as apodization. The transmit beamformer 22 controls focusing and apodization, along with transmit pulse shape in advanced systems. The pulse generator 24 produces a low-voltage transmit pulse waveform, which is amplified by the high-voltage (HV) pulser 14 to the high-voltage amplitudes required to drive the transducer array during transmit.

Received signals are typically first amplified by a fixed gain, low noise amplifier (LNA) (e.g., see linear amplifier 24), further amplified by a time-gain compensation (TGC) amplifier to account for attenuation in tissue that increases exponentially with depth (e.g., see TGC 28) and then (typically in prior art systems) digitized by analog to digital converters (A/Ds) 30. These digitized signals are then focused and apodized by the receive beamformer 18, followed by image processing and scan conversion (e.g., see post processor 32) for display on a monitor 34. Some systems have Doppler circuits to estimate blood flow, whose output is fed to speakers 36 and/or displayed on the monitor 34. The global timing and coordination of the transmit beamformer 22. T/R (transmit/receive) switch 16 and received beamformer 18 are handled by central beamforming control 38.

Figure 2:
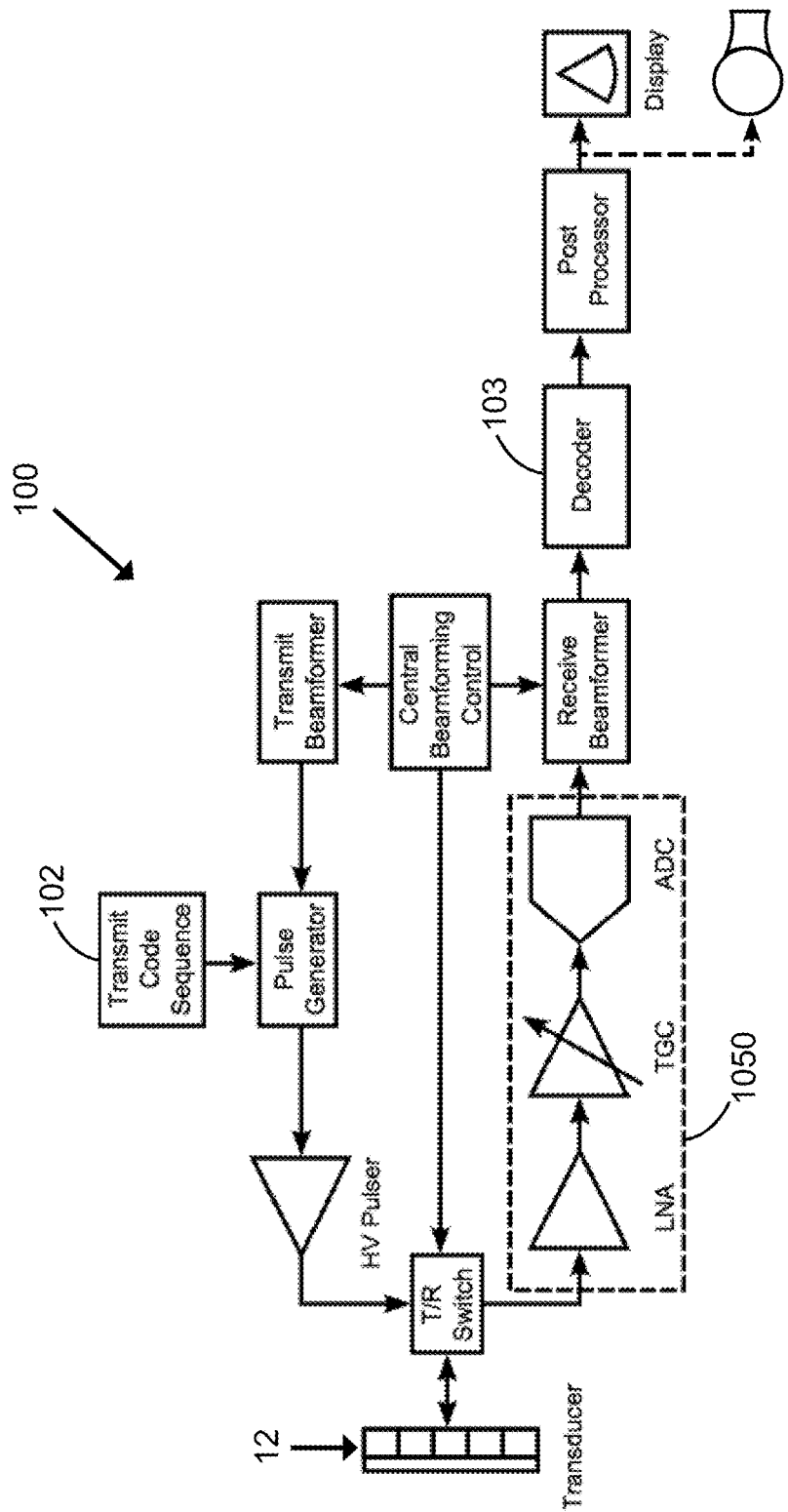
FIG. 2 is a block diagram of an ultrasound system that uses coded excitation.

FIG. 2 is a block diagram of a typical prior art ultrasound system 100 that uses coded excitation of the electrical signals inputted to the transducer array 12. Coded excitation is implemented through the addition of an encoder containing the transmit code sequence 102 and a decoder 103. The transmit code sequence 102 is convolved with the base excitation pulse generated by the pulse generator 24 to form an encoded transmit waveform that is longer than the original base excitation pulse in that consists of a train of scaled replicas of the excitation waveform. The decoder 103 compresses the digitized post-beamformed (i.e., delayed, summed and apodized) received data in such a way that the returning echo signal is shortened to preserve resolution while at the same time preserving the increase in energy provided by the longer pulse. Numerous methods exist to perform the decoding operation, including convolution with a matched filter.

Figure 3:
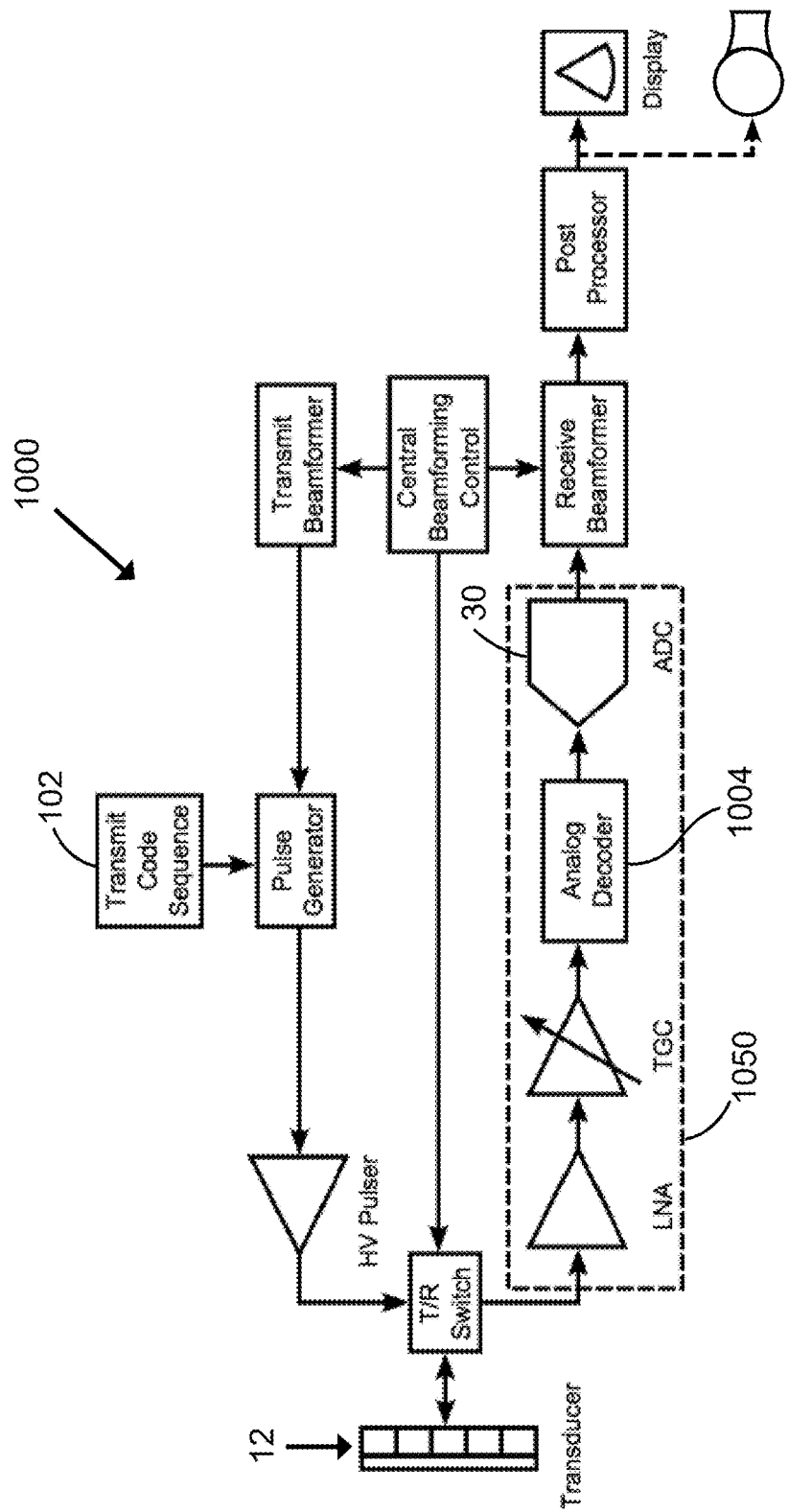
FIG. 3 is a block diagram of an ultrasound system using an analog-domain coded excitation scheme according to an embodiment of the present invention.

FIG. 3 is a block diagram of an ultrasound system 1000 according to an embodiment of the present invention. System 1000 uses coded excitation of the electrical signals inputted to the transducer array 12 wherein the encoding operation can be similar to the prior art methods described in FIG. 2. However, in the system of FIG. 3, after amplifying and filtering the electrical signal received from the transducer 12, the signal is decoded/compressed by analog decoder 1004 prior to analog to digital conversion by A/D converters. Since the decoding operation shortens the received echo signal, significant bandwidth and memory requirements are alleviated for subsequent downstream processes. A/D conversion speed is increased and power consumption is reduced, system-wide memory requirements are relaxed, and the beamforming computations operate on significantly less data. These effects translate to reductions in silicon circuit area and power consumption for every receive channel, and these are important for reducing costs and improving portability.

Figure 4:
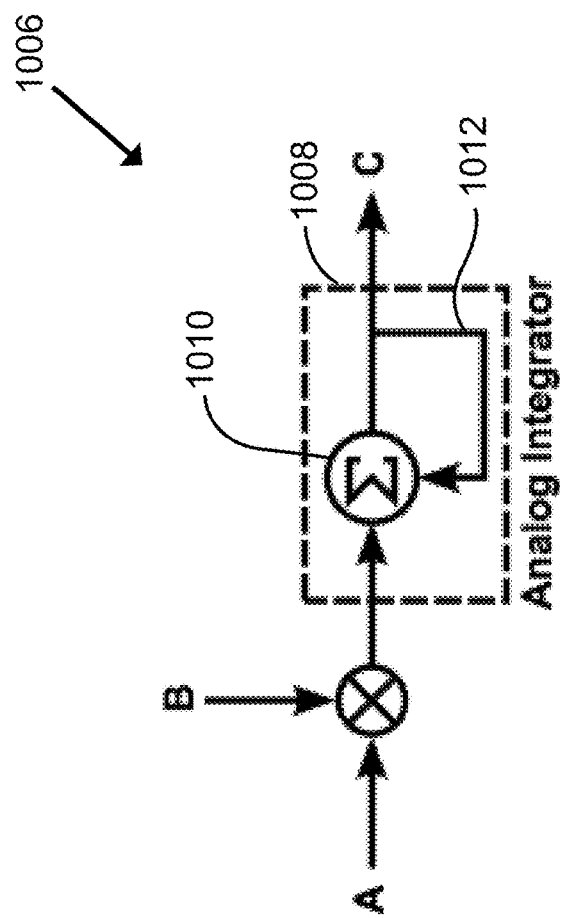
FIG. 4 is a signal diagram illustrating an analog-decoding scheme used according to an embodiment of the present invention.

A signal flow diagram of an analog domain compression filter 1006 according to an embodiment of the present invention is shown in FIG. 4. This compression filter is an embodiment useful for performing the decoding function of analog 1004 according to the present invention. In the embodiment shown in FIG. 4, compression filter 1006 operates in the analog domain. The received ultrasound signal, A, is multiplied by the decoding signal, B. Integrator 1008 in this embodiment includes a summer 1010 with a feedback loop 1012. As the incoming received signal A is multiplied by the compression filter weights B, the product A×B is integrated over the length of the compression filter to yield a single, discrete, analog sample. This sample can subsequently be digitized and later used in conjunction with other decoded samples for beamforming to create an image.

An example of the analog decoding process according to an embodiment of the present invention is shown in the timing diagrams of FIGS. 5A-5B. The received signal A is a sinusoid and decoding signal B is limited to weights from the set {−1 0 1}. The output of the integrator, i.e., signal C, is shown for two cases of the phase relationship between A and the decoding signal, B, with FIG. 5A showing a zero degrees phase shift between signals A and B and FIG. 5B showing a 45 degrees phase shift between signals A and B.

Figure 6:
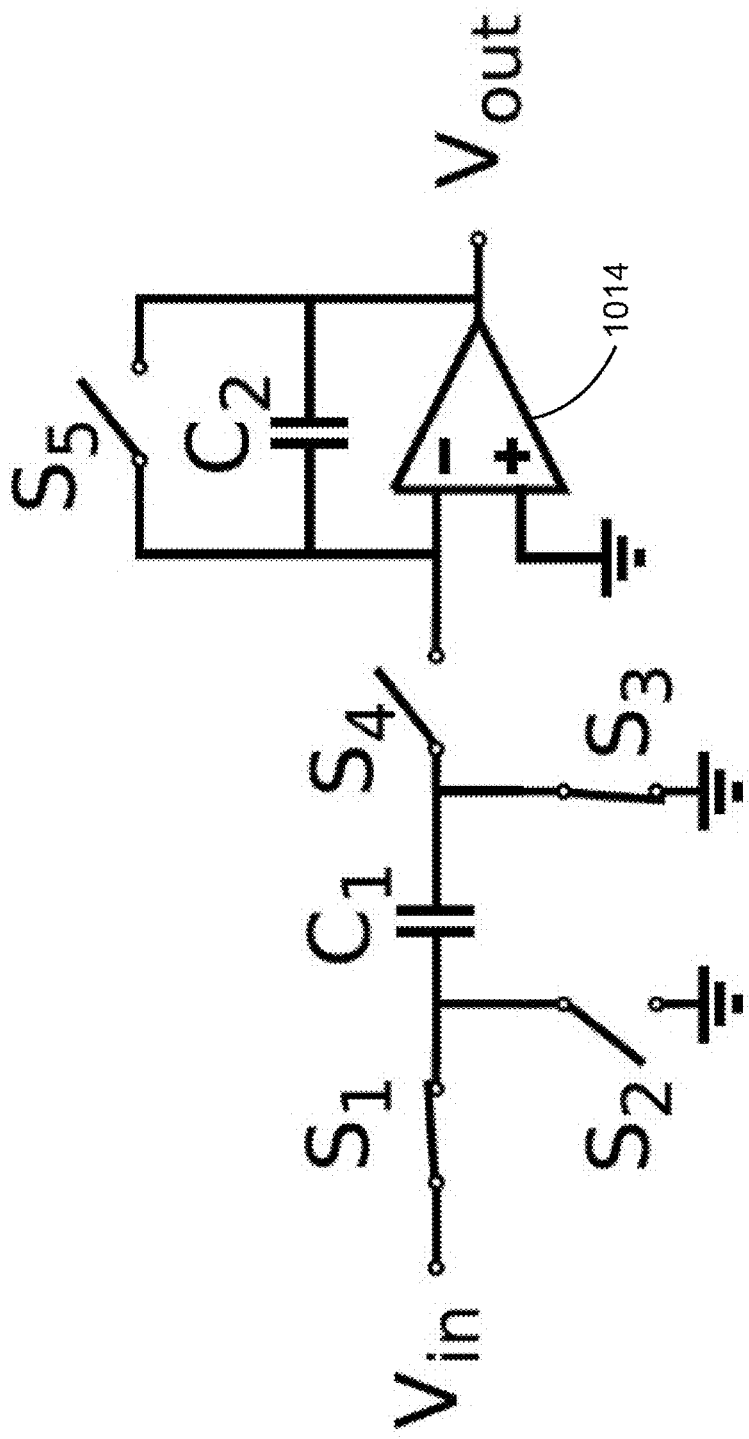
FIG. 6 shows a circuit implementation of an embodiment of the present invention.

FIG. 6 shows a circuit implementation of the decoder illustrated in FIG. 4.

Switches S1-S4, capacitors C1-C2, and an amplifier 1014 are arranged in a classic single-ended, switched-capacitor, discrete-time integrator topology that is robust to parasitics commonly present in integrated circuits. Switch. S5 is added to provide reset capability. This circuit implementation (as well as most other embodiments that follow) combines a sample-and-hold (S/H) unit with a discrete-time analog integrator. A S/H unit, whether it is a separate circuit block or is integrated into the ADC (analog to digital converter) itself, is typically required for digitizing continuous signals. Thus it is both efficient and convenient for the decoding filter to operate in the discrete-time domain, which ties the convolution operation to the sample rate. During the sampling phase of the discrete-time integrator, switches S1 and S3 are closed. The left plate (as illustrated in FIG. 6) of capacitor C1 is driven by the continuous-time signal from the output of the previous stage, for example, the TGC amplifier or anti-aliasing filter. At the time designated for capturing an analog sample which, as alluded to above, can be coincident with the sampling rate, switch S3 opens closely followed by the opening of switch S1. This stores the analog sample on capacitor C1. Next, switches S2 and S4 close, causing the transfer of the charge (stored analog sample) stored on capacitor C1 to capacitor C2. Upon subsequently opening switches S2 and S4, the amplifier and C2 hold the transferred charge, and switches S1 and S3 close in preparation for capturing the next analog sample on capacitor C1 by repeating the process described above. Each subsequent sample is captured on capacitor C1 in the sampling phase and added to the charge on capacitor C2 in the integration phase. Through this process, the charge on capacitor C2 at the end of the integration phase is a function of the sum of all the previous samples. Specifically, the integrator output voltage, $V_{out}$, is approximately:

$$V_{out}(kT) = V_{out}[(k-1)T] - V_{in}[(k-1)T]*(C1/C2) \quad (1)$$

where k is the sample index, T is the sampling interval (time period), and $V_{in}$ is the input voltage to the integrator. It should be appreciated that sampling need not occur at rigid intervals. The analog voltage can be converted to digital form by an analog to digital converter (ADC) 30, stored in digital memory, and later processed for image formation. Switch S5 can be closed to clear the charge on capacitor C2 to reset the integrator in preparation for the next integration cycle.

Figure 7:
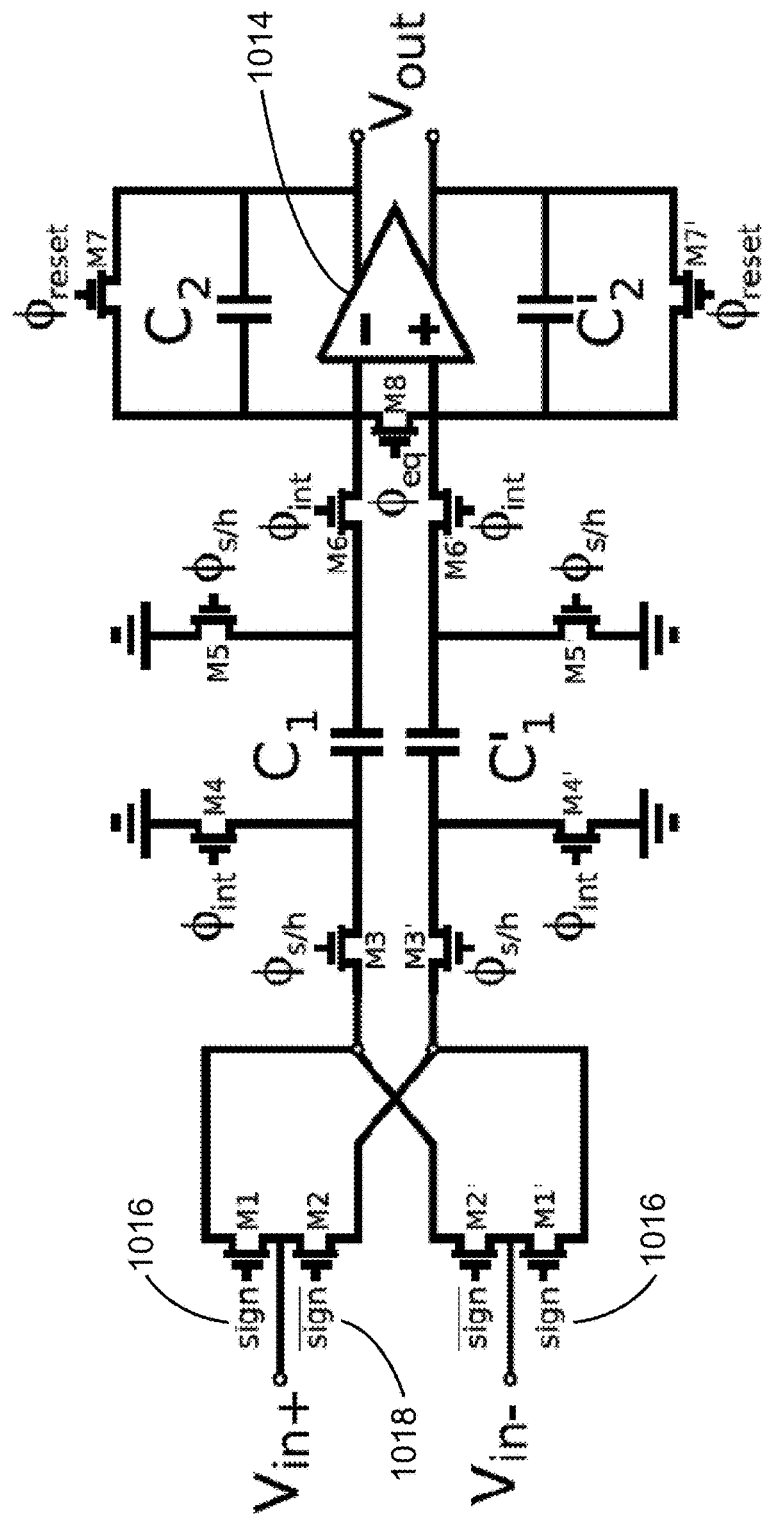
FIG. 7 is a schematic of an embodiment of the present invention.

FIG. 7 illustrates an embodiment of the present invention in which the integrator core illustrated in FIG. 6 has been arranged in a differential configuration and the switches S1-S5 have been replaced by n-type MOSFETs M1-M7. It should be appreciated that the switches S1-S5 can be implemented through other further alternative features, such as p-type MOSFETs, parallel connected n- and p-type MOSFETs, or other transmission gate topologies. It is further noted that although FIG. 7 illustrate the integrator core arranged in a differential configuration, that any or all of the structures/circuits described with regard to the present invention can be implemented with differential signal paths. Thus, a circuit drawn with a single-ended signal path in any of the present Figs. can be alternately implemented in a differential configuration. The circuit topology of FIG. 7 facilitates the reduction of both even-order distortion and common-mode noise sensitivity. Also, offsets introduced by charge injection originating from switching elements are subtracted out from the differential output signal. Still further, the differential topology shown in FIG. 7 enables the simple implementation of coefficient multipliers for two-level codes. Rather than split the data path into two branches with an analog multiplier included in each branch, the polarity of the received signal can be reversed much more efficiently by switching the positive and negative leads at the input of the differential integrator. This is accomplished in FIG. 7 by the switching configuration formed by M1 (M1') and M2 (M2'). Asserting the 'sign' signal implements a '+1' coefficient multiplication, whereas de-asserting the 'sign' signal 1018 (indicated by "sign" with a bar over it in FIG. 7) implements a '−1' coefficient multiplication Thus the overall circuit in FIG. 7 implements the function of analog compression filter 1006 for decoding signals limited to the set {−1 0 1}.

Figure 8:
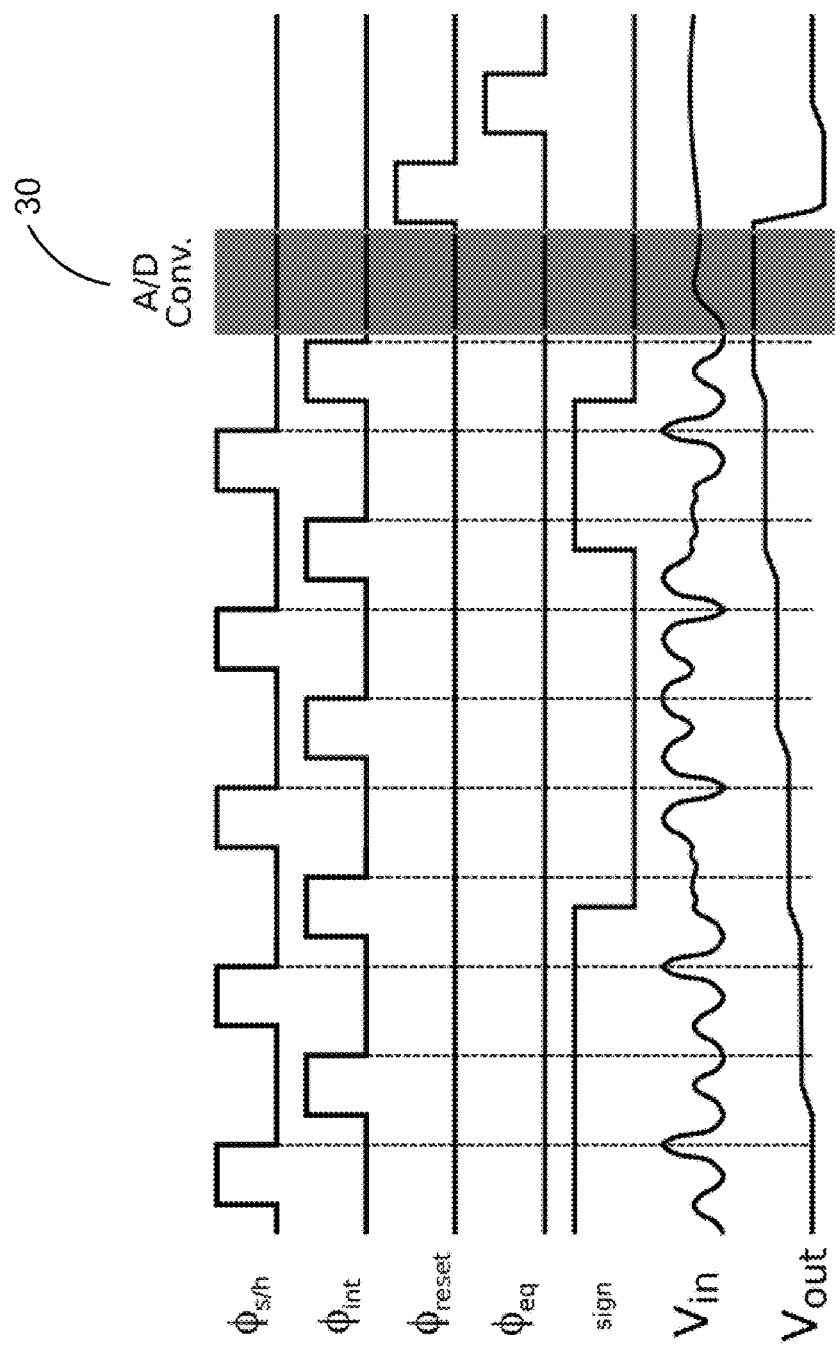
FIG. 8 is a timing diagram of the control signals for the embodiment in FIG. 7.

The control signals for MOSFET devices M3-M8 are simplified to illustrate the operation of the differential discrete-time integrator. An example control signal sequence is shown in FIG. 8. The sampling phase occurs when $\phi_{s/h}$ is asserted and the integration phase occurs when $\phi_{int}$ is asserted. Generally, these two signals are never asserted simultaneously and their edges are non-overlapping. The actual number of control signals that must be asserted from off-chip (i.e., from a location external of the chip on which the circuitry of FIG. 7 is implemented) can be reduced by including simple control and delay logic on-chip (whether it be within each receive channel or globally implemented and shared by multiple receive channels) to enforce these timing constraints. For example, a single control signal could be asserted for sample mode and de-asserted for integration mode.

For the timing diagram in FIG. 8, the analog voltage Vout at the output of the integrator is digitized by an analog to digital converter 30 after all five samples have been acquired and integrated. After digitization, device M7 is turned on to reset the integrator by $\phi_{reset}$. The fixed differential offset associated with the asymmetric charge injections of MOSFET devices M7 and MT can be removed by asserting $\phi_{eq}$ to equalize the offset between the positive and negative signal paths.

Figure 9:
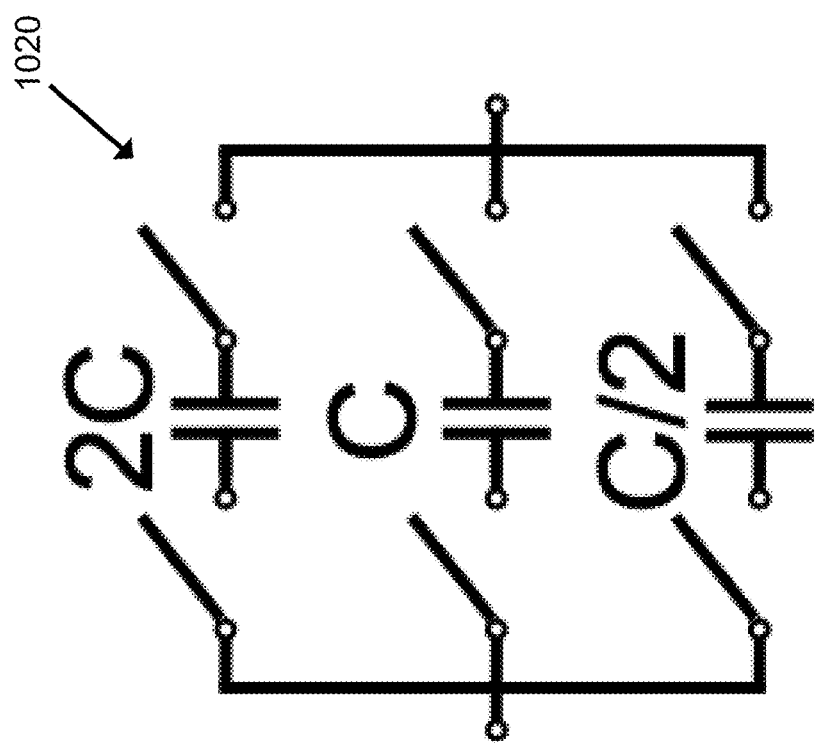
FIG. 9 is a depiction of an adjustable capacitor made up of switchable capacitors according to an embodiment of the present invention.

In an alternative embodiment to that shown in FIG. 7, capacitors C1 and C1' can be provided as parallel-connected, switched capacitors whose capacitance values are chosen to enable realizing codes having more than two levels. FIG. 9 illustrates an embodiment of a switched capacitor 1020 that can be used for such an alternative embodiment. The available coefficients in the code (e.g., decoding signal B in FIG. 4) can be extended, for example, from the binary case of [−1, +1] to [−3.5, −3, −2.5, −2, −1.5, −1, −0.5, 0.5, 1, 1.5, 2, 2.5, 3, 3.5] (or multiples thereof) by adding a second switched capacitor 2C having twice the capacitance of capacitor C and a third switched capacitor C/2 having half the capacitance of capacitor C, in parallel with C1 (shown as "C" in FIG. 9). The switching of these capacitors 2C, C and C/2 can be actuated dynamically in response to changes in the excitation code between transmits, or, alternatively can be fixed/hard-coded if the code is permanent. A person of ordinary skill in the art will recognize these and other circuit modifications to account for other coefficient implementations.

Also, since equation (1) indicates that $V_{out}$ is a function of the relative values of C1 and C2 in FIGS. 6 and 7, the ratio C1/C2 should be chosen to prevent saturation of the integrator. Optionally, the system may be configured so that the ratio is tunable to adjust for different code lengths at run time (e.g. using the scheme in FIG. 9). The embodiments of the present invention that offer the differential configurations for accepting variations in excitations codes/decoding codes, in addition to the advantages provided by the differential configuration, also provide advantages by the efficiencies resultant from conserving circuit area independent of code length.

Further alternative embodiments are configured to balance the tradeoffs associated with power, speed, mismatch (which refers to random variations in the physical dimensions of CMOS (complementary metal oxide semiconductor) devices during fabrication) or other parameters in addition to area. For example, power or area constraints might limit the speed of the amplifier in the integrator, especially for higher center frequencies. The charge transfer speed in a switched capacitor implementation might also be too slow for high bandwidth signals. Therefore, several alternative embodiments are possible to implement the analog-domain decoding scheme under various area-power-speed constraints.

Figure 10A:
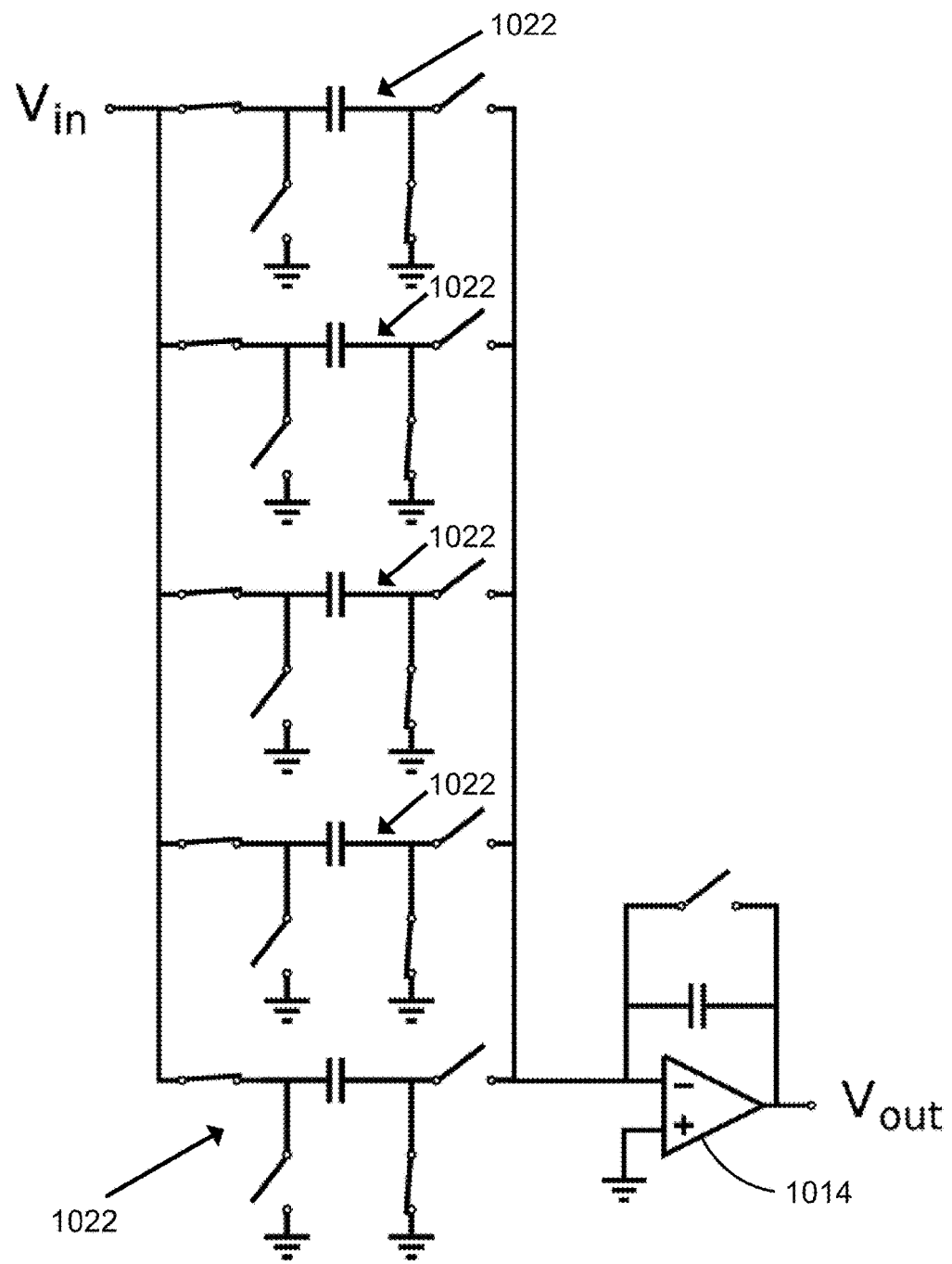
FIG. 10A illustrates an embodiment in which a sampling portion of a circuit is replicated and integration can be performed under a relaxed time constraint after the entire encoded signal has been acquired.
Figure 10B:
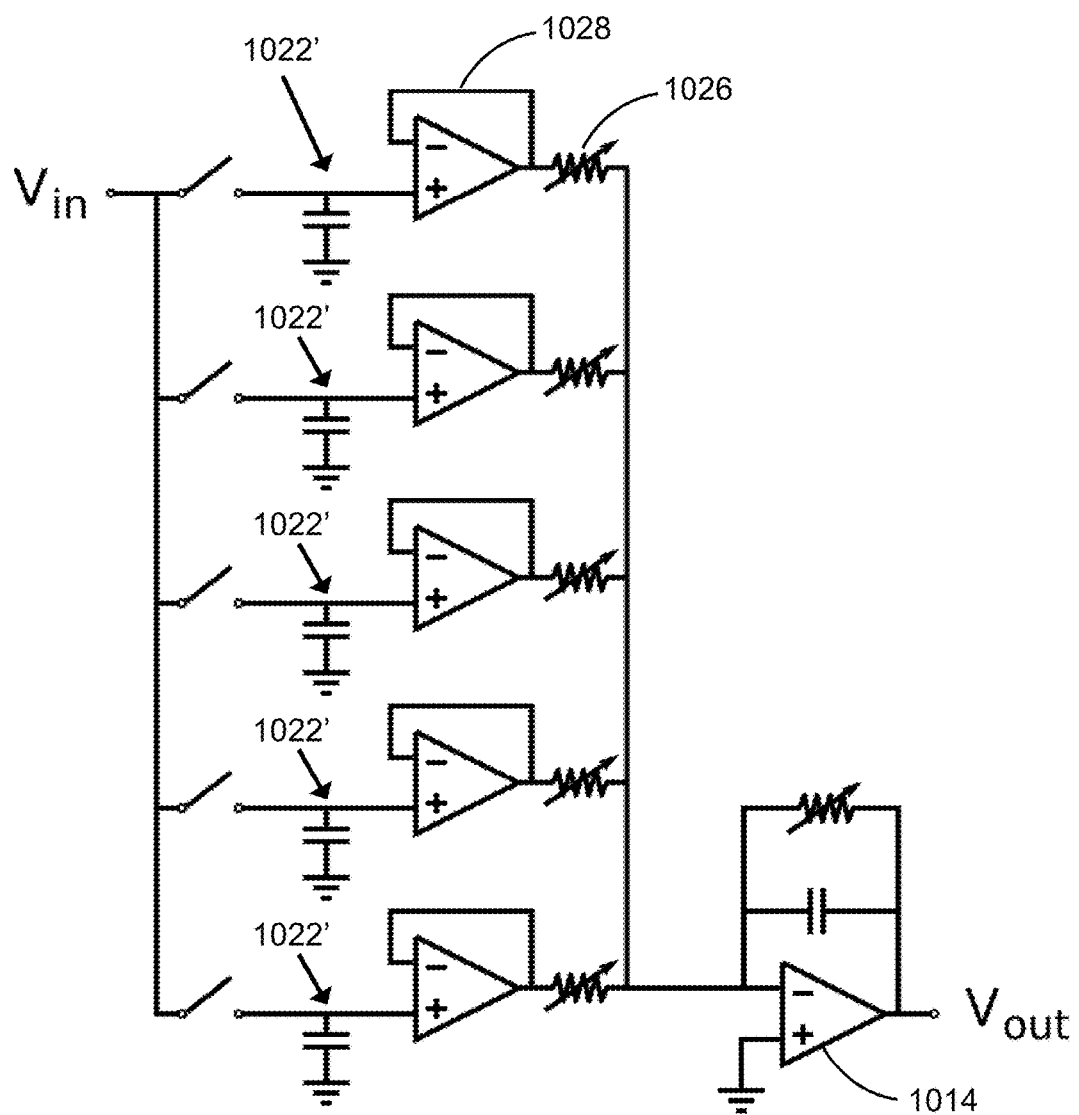
FIG. 10B illustrates an embodiment of the invention in which multiple sample-and-hold units (with unity-gain output buffers) are arranged into a summing amplifier configuration.
Figure 11:
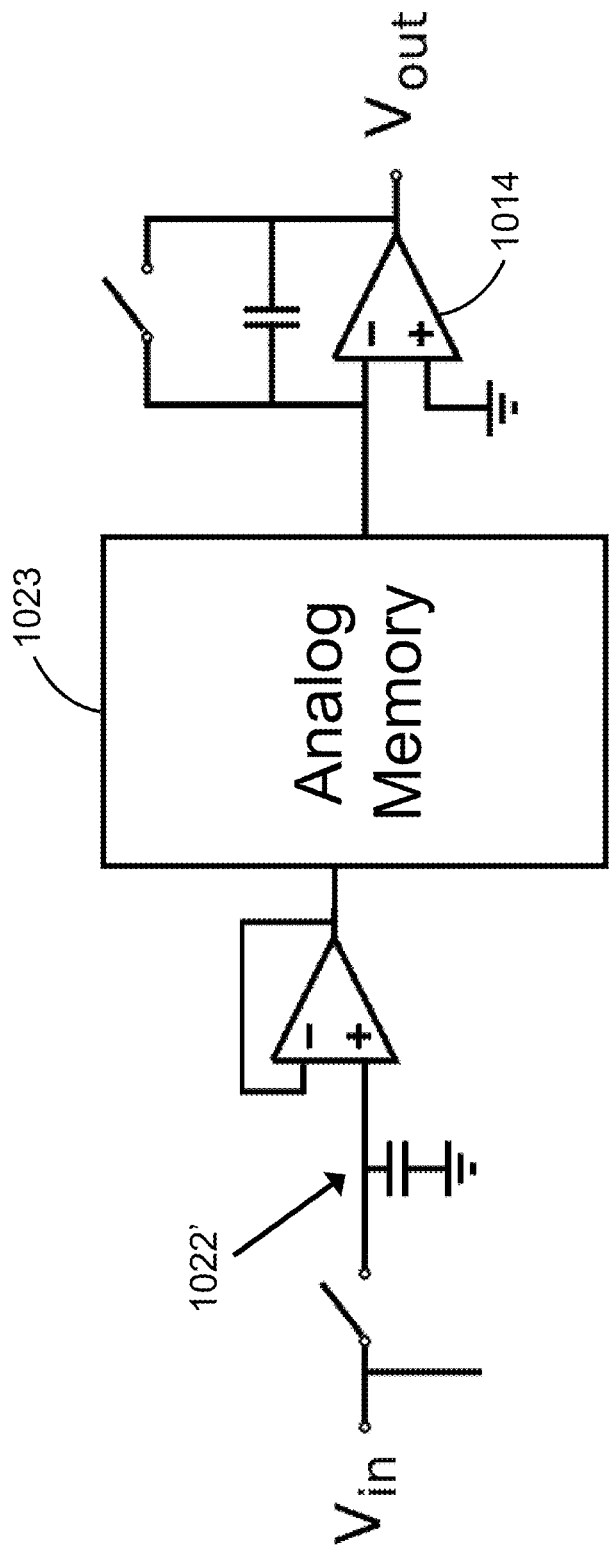
FIG. 11 Fig. illustrates an embodiment of the invention in which a single sample-and-hold unit is used in conjunction with an analog memory bank that holds every sample over the entire code length.

An S/H unit 1022 or 1022' may be provided for every sample over the entire code length, as is illustrated in the embodiments of FIG. 10A and FIG. 10B. Alternatively, an analog memory bank 1023 can be provided to hold every sample over the entire code length, as illustrated in FIG. 11. The received echo signal is initially sampled by S/H unit 1022' which, in turn, outputs each captured sample to the analog memory 1023 where it is temporarily stored. With these embodiments, rather than integrate the current sample prior to acquiring the next sample, the integration does not occur until all samples from an entire encoded, received echo signal have been acquired. The number of samples that are acquired depends on system requirements. For example, a typical B-mode ultrasound system may need to capture hundreds of samples per channel per transmit event. The provision of an S/H unit 1022, 1022' for every of the samples in such an example, or even the implementation of a sufficiently large analog memory 1023 might be impractical for some types of systems, particularly portable ones. However, these embodiments are much more practical for a C-mode ultrasound system, such as a low-cost, portable, C-mode ultrasound system that only need to capture a few samples per channel per transmit event. Although the embodiments of FIGS. 10A-11 are typically less practical for B-mode ultrasound systems, they are still capable of being implemented with such systems, and the present invention includes such implementations.

In the embodiments of FIGS. 10A, 10B and 11, once the samples are acquired, they are then integrated sequentially through multiplexing in conjunction with switched capacitor techniques (as in FIG. 10A) or the sample and hold (S/H) units 1022' can be connected in parallel to an operational amplifier in a summing amplifier configuration (as in FIG. 10B, for example), or acquired from memory 1023 in a sequential or parallel manner. This provides a much longer time interval over which the integration can be performed, relative to previous embodiments described. Thus, if an amplifier has adequate speed to perform integrations using the iterative methods described above, a relatively slower amplifier 1014 can be used in the configurations of FIGS. 10A, 10B and 11 for processing the same samples by the techniques described for FIGS. 10A, 10B and 11. Also, if the amplifier 1014 used in FIG. 6 or 7 is too slow to keep up with iterative integration processes for a particular use, (e.g., samples cannot be integrated fasted enough), then the amplifier 1014 may still be adequate to perform successfully in the arrangements shown in FIG. 10A, 10B or 11 for the same use.

Furthermore, amplifier 1014 can be shared by multiple S/H units 1022, 1022' within each receive channel or the integrating amplifier can be located outside the receive channels and shared by multiple channels in a row, column, or other multiplexing arrangement. The potential benefits of such an arrangement include reduced power consumption and mismatch as well as more rapid sample acquisition.

In FIG. 10A, the capacitance value of each hold capacitor 1024 can be chosen (or made adjustable, as in FIG. 9 or some other means) to correspond to any desired code coefficient. Similarly, the resistance values of the resistors 1026 connected between the unit-gain voltage followers 1028 and the integrator in FIG. 10B can be chosen (or made adjustable) to correspond to any desired code coefficient.

Figure 12:
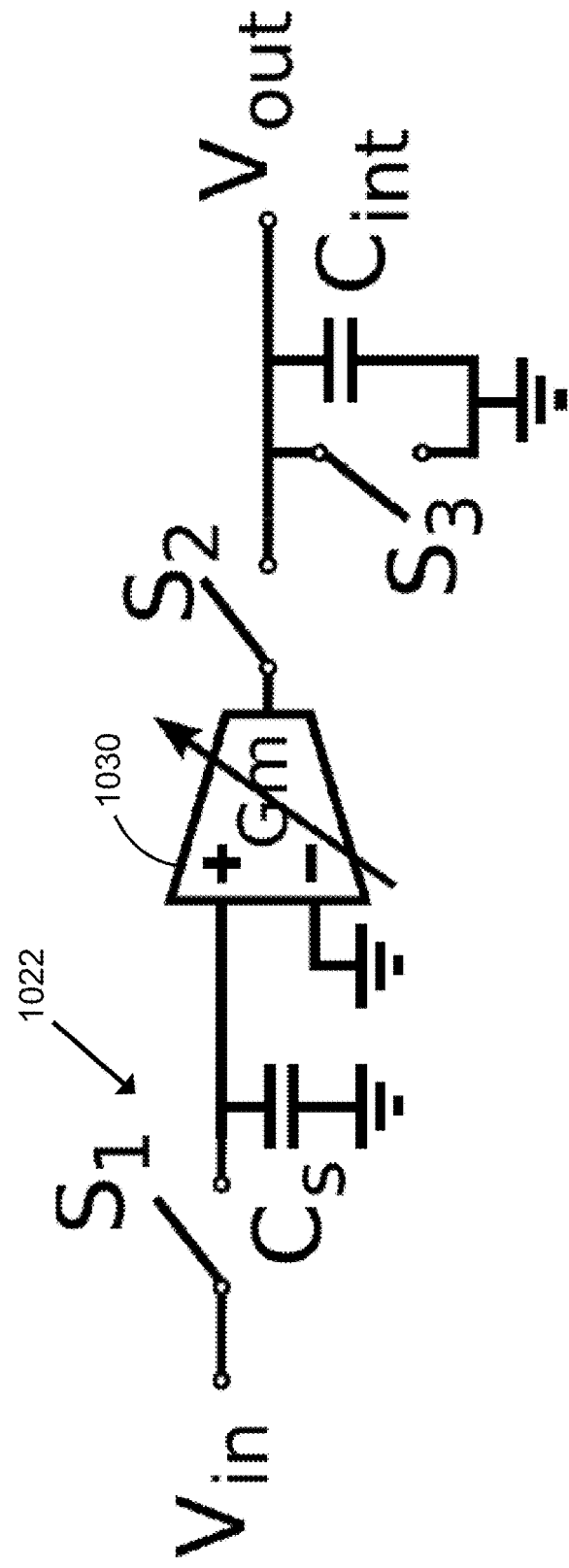
FIG. 12 illustrates a sample-and-hold unit followed by an integrator constructed from an adjustable transconductor and capacitor according to an embodiment of the present invention.

Alternatively, the integrator can be implemented by using a transconductance (Gm) amplifier 1030 in conjunction with a capacitor Cint, as illustrated in FIG. 12, instead of the switched capacitor implementations used in FIGS. 6, 7 and 10A-10B or the operational amplifier implementations in FIGS. 10B-11. This alternative integrator is implemented in FIGS. 12 and 13. In FIG. 12, S/H unit 1022 comprising switch S1 and capacitor $C_S$ feeds into the input of a transconductance amplifier 1030. Integration takes place when switch S2 closes for a specified period of time, delivering a current (linearly related to the input voltage stored in the S/H 1022) onto the integration capacitor, $C_{int}$. The time period over which S2 remains closed is chosen to avoid saturation of $C_{int}$ and to meet settling and bandwidth constraints. The voltage on $C_{int}$ can be expressed approximately as:

$$V_{out} = (I_{out}/C_{int}) * \Delta t \qquad (2)$$

where $\Delta t$ is the length of time S2 is closed.

Figure 13:
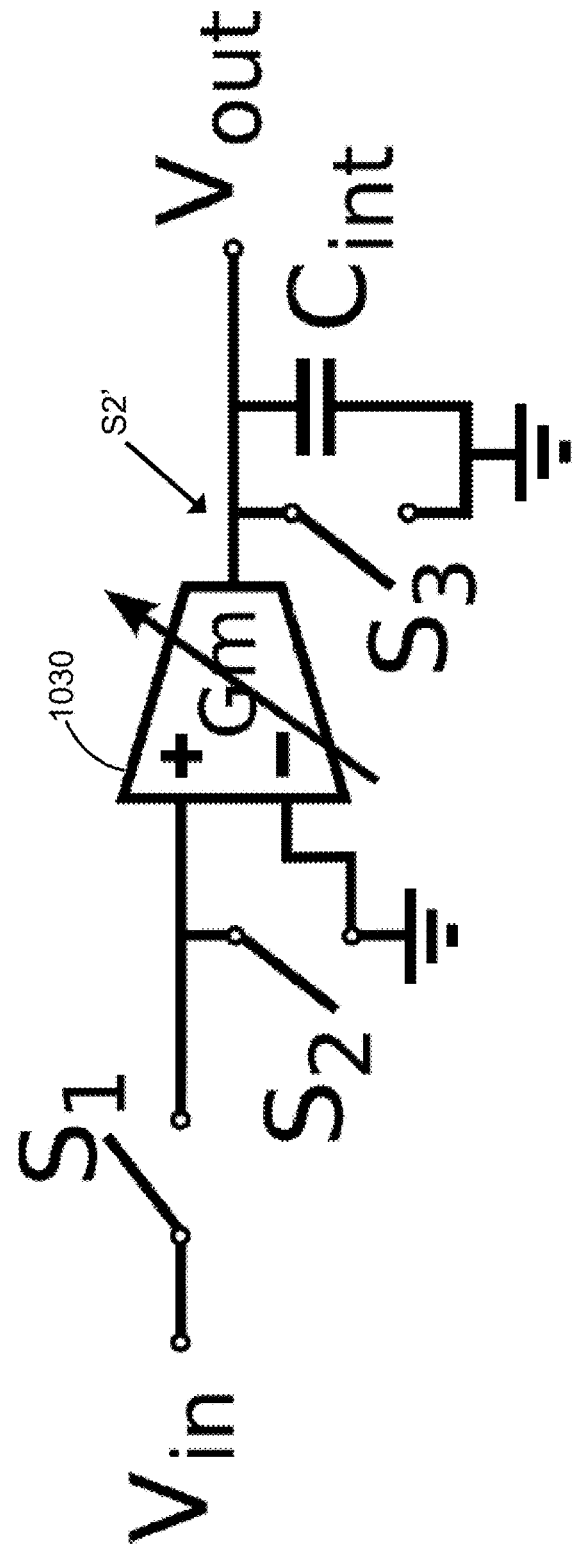
FIG. 13 illustrates a modification of the circuit shown in FIG. 12 to eliminate the hold capacitor at the input according to an embodiment of the present invention.

In the embodiment of FIG. 13, the capacitor Cs has been eliminated from the configuration shown in FIG. 12. The elimination of the capacitor $C_S$ has the added benefit of providing a more compact implementation and reducing the capacitive load experienced by the circuit component driving $V_{in}$. Ideally, when switch S1 is open and switch S2 is closed, the charge stored on $C_{int}$ is unaffected by the transconductance amplifier 1030 (output current is substantially zero) and the integrated voltage is retained in between integration periods. In practice, the transconductance amplifier 1030 might need to be deliberately placed in a high-impedance state instead of, or at the same time as, the closing of switch S2. This high-impedance state can be imposed by adding a series switch S2' at the output of transconductance amplifier 1030 and prior to the switch S3 in the same manner that switch S2 is positioned in FIG. 12 at the output. Otherwise, the transconductance amplifier needs to be designed to have little or no offset such that the output stage neither sources nor sinks current when the inputs are shorted.

In the embodiments of FIGS. 12 and 13, switch S3 is used to reset the integrator in between decoding cycles. Also, the transconductance, Gm, of the transconductance amplifier 1030 can be made adjustable to correspond to any desired code coefficient. A person skilled in the art would recognize multiple methods for implementing this adjustability of the transconductance, including real-time analog and digital methods.

It is further noted that the integration time period, Δt, can be dynamically adjusted to enable arbitrary code weights/coefficients without the need for area consuming circuit components such as the tunable capacitor bank 1020 of FIG. 9 or the need for an adjustable transconductance, Gm of transconductance amplifier 1030.

The embodiments of FIGS. 12 and 13 provide an advantage over switched-capacitor techniques in that they provide a relatively more compact implementation and relatively faster operation, since the circuits of these embodiments operate in a current-mode regime as opposed to a voltage or charge-transfer regime.

With regard to transducer arrays 12, it is noted that the embodiments of the present invention can be implemented individually on the signal received from each element, or on the beamsum obtained by apodizing and focusing the signals received from multiple elements.

In other embodiments, the present invention is configured for use in C-scan imaging. In medical applications, C-scans are images of tissue in a plane that is parallel to the surface of the skin. Note that the C-scan imaging plane is perpendicular to the conventional cross-sectional B-scan imaging plane. One method of creating C-scan images is detailed in U.S. patent application number 2007/0016022, which is assigned to the University of Virginia Patent Foundation and which is hereby incorporated herein, in its entirety, by reference thereto.

Figure 14:
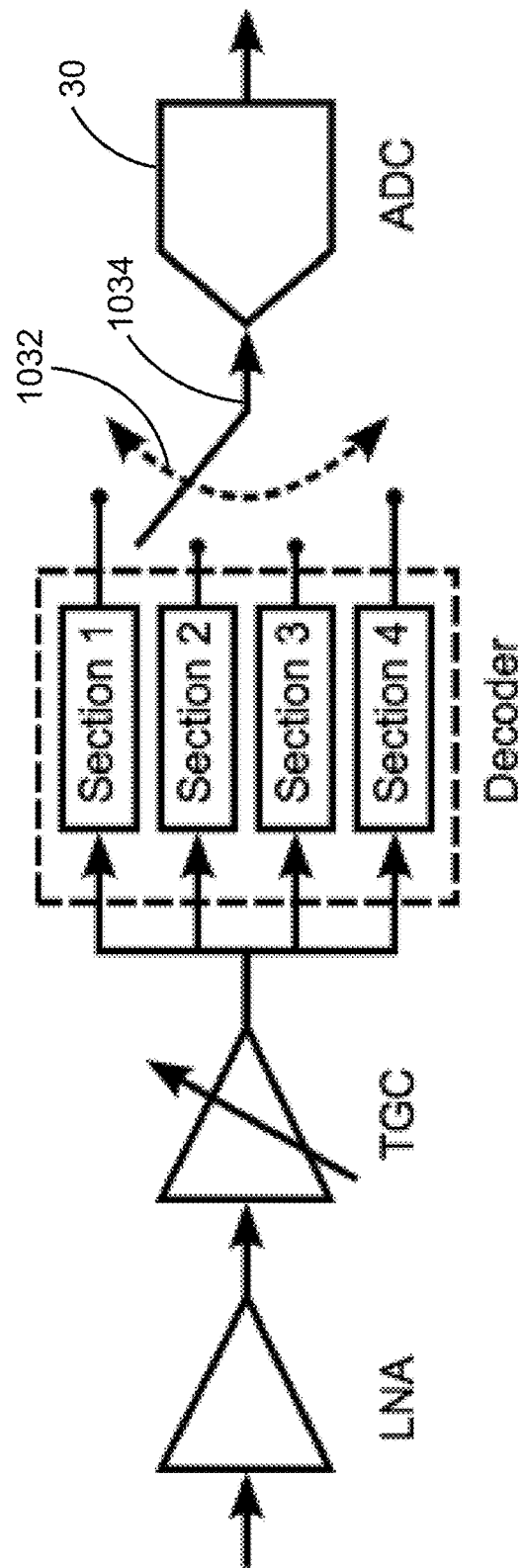
FIG. 14 illustrates a system of which the receive channels use four decoding sections to yield four unique decoded output samples per channel according to an embodiment of the present invention.

FIG. 14 illustrates an embodiment of the present invention configured for C-scan imaging. The blocks labeled Section 1-Section 4 each contain either the circuit shown in FIG. 7 or variations of it, and thereby yield in total four unique decoded output samples per channel.

Each output sample is constructed using k received samples, where k is the length of the decoding filter. These k samples are each weighted by their respective filter coefficients and integrated 1032 to yield one decoded output sample 1034.

The decoded output sample 1034 is subsequently digitized by ADC 30 and then apodized and focused to construct C-scan images as described in U.S. patent application number 2007/0016022. It should be appreciated that there are many ways to form C-scan images, and that C-scans may be formed using an arbitrary number of samples and many different focusing methods.

Figure 15:
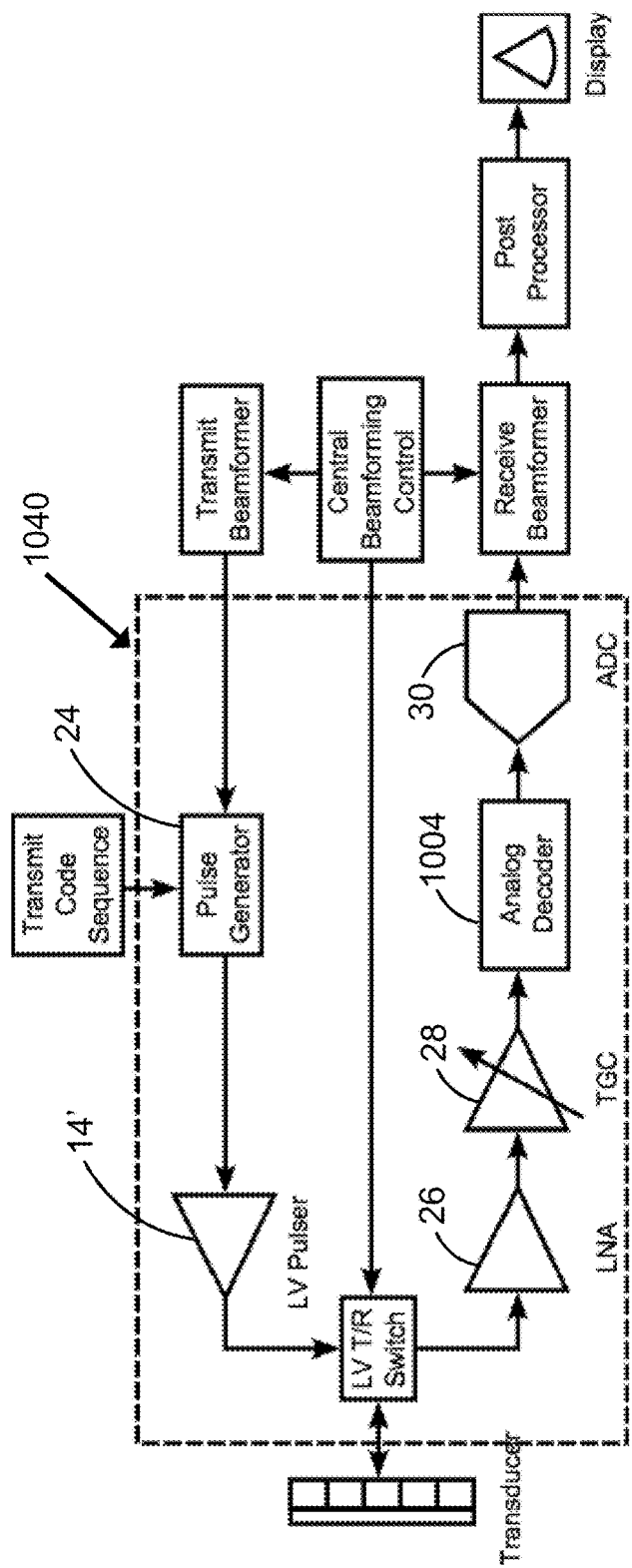
FIG. 15 is a high-level diagram of a single integrated circuit "cell" that comprises transmit and receive circuitry for a single channel according to an embodiment of the present invention.

If the use of coded excitation improves SNR beyond a system's minimum requirements for SNR, it could the allow the excitation of the transducer 12 with a relatively lower magnitude electrical pulse. In this case, the use of coded excitation offsets the loss in SNR that would typically ensue when the pulse magnitude is lowered. This, in turn, relaxes the requirements of the receive protection circuit needed to protect the sensitive receive circuits from a much lower magnitude excitation pulse. Moreover, the excitation pulse may be lowered enough to combine the transmit circuits (which includes pulse generator 24 and the low-voltage puller 14') along with the sensitive receive circuits (each of which includes LNA 26, TGC 28, analog decoder 1004 and ADC 30) onto a single chip 1040, as shown in FIG. 15, in contrast to locating the transmit circuits off of the chip 1050 on which the receive circuits are located, e.g., see FIGS. 1-3. This combined configuration on a single chip as illustrated in FIG. 15 provides significant savings in terms of cost and system size because the number of bulky and expensive high-voltage, off-chip components is reduced or even eliminated. Note that the low-cost, portable C-mode systems described above contain a single off-chip transmit circuit, which means only a planar, non-focused transmit is possible. The high-channel count of such a system is too high to provide an off-chip transmit circuit for every transducer element because of interconnect complexity and the large cost, power and circuit board area consumed by so many high-voltage components. However, by moving the transmit circuits on-chip as described, along the receive circuits enables every transducer element to be driven by a unique transmit circuit. With this arrangement, focusing and steering on transmit are possible. These capabilities, as well as the capabilities associated with unique encoding on an element-by-element basis, are significant improvements over the prior art.

Figure 16:
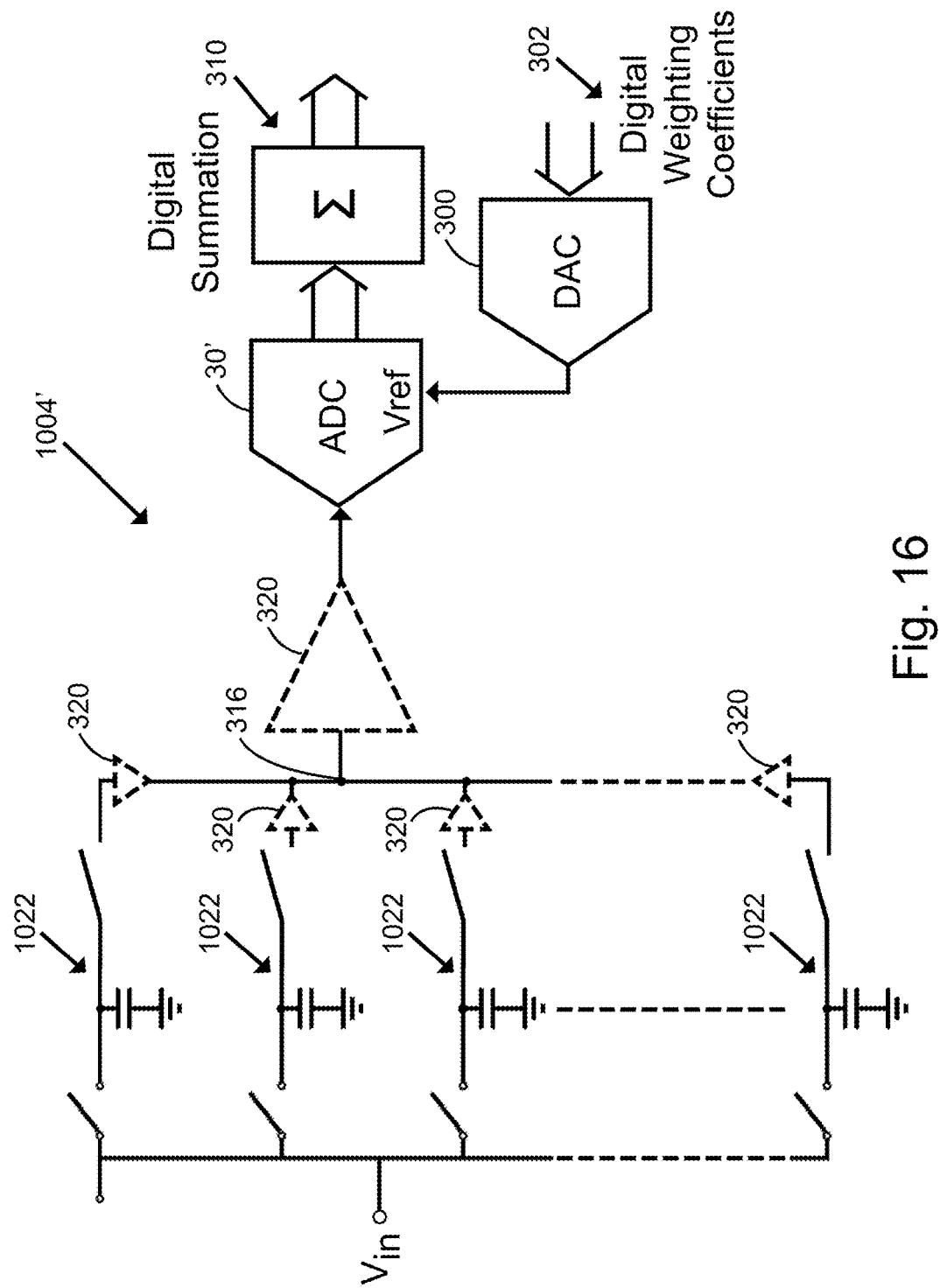
FIG. 16 shows a schematic circuit of a mixed signal decoder according to an embodiment.

Alternative to using an analog decoder 1004, a mixed signal decoder 1004' can be used to provide the same advantages described herein with regard to the analog decoder. FIG. 16 shows a schematic circuit of a mixed signal decoder 1004' according to an embodiment of the present invention. Mixed signal decoder 1004' can be used in place of analog decoder 1004 and ADC 30 in FIGS. 3 and 15, for example.

A set of sample-and-hold (S/H) circuits sequentially sample a received signal during a code length. Although FIG. 16 shows use of S/H units 1022 (like in FIG. 10A), it is noted that, alternatively, S/H units 1022' could be used like in FIG. 10B, or an arrangement like that shown in FIG. 11 (i.e., 1022' and 1023) could be used. After sampling, the individual samples are presented to an ADC 30'. A reference signal for the ADC 30' is inputted from a digital-to-analog converter (DAC) 300 converter which is loaded with coefficient data 302 in synchronization with the switching of the individual S/H signals to the ADC 30'. In this manner, the weight of the individual samples is adjusted by the scaling of the ADC 30' transfer characteristic controlled by the DAC 300 output that is inputted to ADC 30'. The ADC 30' outputs decoded digital samples which are summed sequentially in a digital accumulator 310. The output of the DAC 300 can be multiple signals to include both gain and offset information for offset correction and gain scaling prior to summation. The samples are shown as single ended but can, alternatively, be differential. Differential signals enable easy modification of sample sign by switching of the differential nodes as in previously described embodiments. The scaling can also occur by sequentially controlling the gain of the pre-ADC buffer and then summing digitally post-ADC 30'.

Buffer 320 may optionally be provided between switching circuit(s) 1022, 1022', but is not required. Alternative to the embodiment just described, the weighting can be performed in buffer 320 and then weighted analog samples can be inputted to ADC 30.

A buffer 320 may also be optionally included after each individual S/H 1022, 1022', but is not required. If buffers 320 are not included after each individual S/H 1022, 1022', care must be taken to avoid charge sharing during sequential connections to the ADC 30'. Typically the common node 316 after the S/H decoder will be reset between each connection to a known potential.

In another embodiment, the digital summation block 310 can also include digital scaling circuitry to avoid using the DAC 300. In this case the digital weighting coefficients will control digital scaling prior to summation. In this, as well as in other embodiments described, the weighting coefficients can be distributed globally or per channel. Likewise, the DAC 300 can alternatively be implemented globally or per channel in any of the embodiments, as can the ADC 30' and digital summer 310. These are area/speed/power tradeoffs that are well understood by one of ordinary skill in the art.

In addition to coded excitation, the decoding techniques of the present invention can also be used to implement a matched filter to increase SNR, provide bandwidth restriction for use in frequency compounding, or be used in the context of harmonic imaging for improved tissue contrast.

The present invention can be used to solve a separate challenge in low-cost 2D array systems. Specifically, current implementations of low-cost transducers may have the transducing material mounted on a glass reinforced plastic (GRP), or similar, thin planar material. This gives rise to the potential for reverberant, spurious, ("aberrant") echoes contaminating the otherwise ideal received echo signals. The present invention can be modified to partially mitigate the problem of delayed and scaled replicas of the actual echoes occurring a short time after the intended ("real") echoes. For example, with a reverberation signal occurring about 1 μs after the "real" signal (from the echoes of interest not caused by reverberation) and wherein the reverberation signal is scaled by a +0.1 ratio with respect to the "real" signal, the decoding or finite impulse response (FIR) filter weights associated with the timing of these signal events can be set to values of (−0.1, 1) with a time interval of 1 μs between samples. In this way, the reverberant signal (i.e. that resulting from residual (+0.1 scaled) signal 1 μs before the intended signal) is at least partially canceled.

It is further noted that the present invention can be used not only in ultrasound applications (medical, NDE, or otherwise), but also in other pulse-echo imaging applications such as RADAR and SONAR. While the general technique of coded excitation has already found use in these areas, the proposed analog domain decoding scheme and associated embodiments would specifically benefit high channel-count systems and/or those systems with significant cost, size, or energy constraints. Similarly to the C-scan imaging device described above, the invention could allow bulky and expensive off-chip components to be brought on-chip, and/or it could allow reductions in digitization rates and efficient power duty cycle schemes to save energy.

Further, the present invention can also be extended for use in non-imaging applications such as telecommunications, sensor networks, or other situations where achieving high SNR is a tight tradeoff against cost, size or energy constraints.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A pulse-echo imaging system comprising:
a pulse generation circuit configured to provide electrical signals representative of a transmit code sequence;
a transducer configured to receive the electrical signals provided by the pulse generation circuit as pulses using coded excitation according to said transmit code sequence, and to transduce said electrical signals to pulses of energy other than electrical signals; said transducer being further configured to receive echoes of said pulses of energy other than electrical signals and convert the echoes to received electrical signals; and
a receive circuit configured to:
   receive said received electrical signals;
   perform analog sampling of the received electrical signals;
   perform analog decoding of the received electrical signals using information about the coded excitation and using an analog decoder circuit; and
   provide a weighted, summed digital signal using information obtained from the analog sampling and the analog decoding;
processing circuit configured to;
   receive weighted sum digital signal; and
   generate image using the digital signal;
display coupled to processing circuit to display the image.

2. The system of claim 1, wherein said receive circuit weights said analog samples, sums said weighted analog samples and converts a resulting summed, weighted analog signal to a summed, weighted digital signal.

3. The system of claim 1, wherein said analog decoder circuit comprises a two-level filter.

4. The system of claim 3 wherein said analog decoder circuit further comprises a switch and a summing device;
wherein the received electrical signals are directed down two circuit paths of said two-level filter, wherein scaled samples are produced by one of said two circuit paths analog multiplying the signals by +1 and the other of the two circuit paths analog multiplying the signals by −1, and, depending upon whether a resulting signal coefficient is +1 or −1, said switch selects one of the circuit paths and passes the scaled sample to said summing device; and
wherein said summing device sums the scaled samples received to yield a decoded sample.

5. The system of claim 1, wherein said receive circuit comprises:
a single-ended circuit implementation having two parallel branches, each containing an analog coefficient multiplier;
one of said branches comprising an inverting unity gain amplifier and the other of said branches comprising a non-inverting unity gain amplifier;
a switch or transmission gate configured to select one of said branches based upon a filter coefficient assigned by said amplifiers;
the selected branch feeding into a single-ended sampling switched-capacitor integrator with reset capability that samples a continuous signal during one phase to provide a sampled signal and adds the sampled signal to previous sampled signals during a subsequent phase.

6. The system of claim 1, wherein said receive circuit comprises a differential circuit, said differential circuit comprising:
a switching circuit that implements positive and negative coefficients by interchanging positive and negative terminals of differential branches of said differential circuit; and
a differential sampling, switched capacitor integrator with reset capability configured to sample a continuous signal during one phase to provide a sampled signal, and, in a second phase, to add the sampled signal to previous sampled signals.

7. The system of claim 1, wherein said receive circuit comprises more than two parallel circuit paths, a switching device and a summing device;
wherein the received electrical signals are directed down the more than two circuit paths, wherein scaled samples are produced by said more than two circuit paths, each containing an analog multiplier having a gain set to provide multiple arbitrary filter coefficients where each branch assigns a different filter coefficient, and, depending upon the resulting signal coefficient, said switch device selects one of the circuit paths having a predefined one of the filter coefficients and passes the scaled sample from the selected circuit path to said summing device;

wherein said summing device sums the scaled samples received to yield a decoded sample.

8. The system of claim 1, wherein said receive circuit comprises:

a single-ended circuit implementation having two parallel branches, each containing an adjustable sampling capacitor;

each said adjustable sampling capacitor being adjustable for multiple different coefficient values configured for decoding coded excitation signals using different codes.

9. The system of claim 1, wherein said receive circuit comprises a differential circuit, said differential circuit comprising:

a switching circuit capable of implementing more than two different filter coefficients by interchanging positive and negative terminals of differential branches of said differential circuit and by providing each differential branch with an adjustable sampling capacitor that is adjustable for multiple different coefficient values; and a differential sampling, switched capacitor integrator with reset capability configured to sample a continuous signal during one phase to provide a sampled signal, and, in a second phase, to add the sampled signal to previous sampled signals.

10. The system of claim 1, wherein said receive circuit comprises:

a plurality of sample and hold circuits, each configured for sampling and holding one sample of the received electrical signals over one code length; and a switched-capacitor integrator configured to commence integration and integrate said samples after all samples from an entire received pulse have been acquired by said sample and hold circuits.

11. The system of claim 1, wherein said receive circuit comprises:

an analog memory bank provided for holding each sample of the received electrical signals over one code length; and a switched-capacitor integrator configured to commence integration and integrate said samples after all samples from an entire received pulse have been held by said analog memory bank.

12. The system of claim 10, wherein a charge storage capacity of each of said sample and hold circuits is set as a function of a predefined filter coefficient, respectively.

13. The system of claim 11, wherein said analog memory bank comprises a plurality of memory cells each having a charge storage capacity, wherein said charge storage capacity of each of said memory cells is set as a function of a predefined filter coefficient, respectively.

14. The system of claim 10, wherein each said sample and hold circuit comprises an adjustable sampling capacitor, each said adjustable sampling capacitor being adjustable for more than two different coefficient values.

15. The system of claim 1, wherein said receive circuit comprises:

a plurality of sample and hold circuits, each configured for sampling and holding one sample of the received electrical signals over one code length; and an operational amplifier configured as a summing operational amplifier, configured to commence integration and integrate said samples after all samples from an entire received pulse have been acquired by said sample and hold units.

16. The system of claim 1, wherein said receive circuit comprises:

an analog memory bank provided for holding each sample of the received electrical signals over one code length; and an operational amplifier configured as a summing operational amplifier, configured to commence integration and integrate said samples after all samples from an entire received pulse have been held by said analog memory bank.

17. The system of claim 1, wherein said receive circuit comprises:

a single-ended circuit implementation having two parallel branches, each containing an analog coefficient multiplier;

one of said branches comprising an inverting unity gain amplifier and the other of said branches comprising a non-inverting unity gain amplifier;

a switch or transmission gate configured to select one of said branches based upon a filter coefficient assigned by said amplifiers;

the selected branch feeding into an input of an integrator comprising a transconductance amplifier and an integrating capacitor, wherein said transconductance amplifier converts charge received through said switch or transmission gate into current and said current is inputted to said integrating capacitor.

18. The system of claim 1, wherein said receive circuit comprises a differential circuit, said differential circuit comprising:

a switching circuit that implements positive and negative coefficients by interchanging positive and negative terminals of differential branches of said differential circuit; and an integrator comprising a transconductance amplifier and an integrating capacitor, wherein said transconductance amplifier converts charge received from said switching circuit into current and said current is inputted to said integrating capacitor.

19. The system of claim 7, wherein said summing device comprises an integrator comprising a transconductance amplifier and an integrating capacitor.

20. The system of claim 1, wherein said receive circuit comprises:

a single-ended circuit implementation having two parallel branches, each containing an analog coefficient multiplier;

one of said branches comprising an inverting unity gain amplifier and the other of said branches comprising a non-inverting unity gain amplifier;

a switch or transmission gate configured to select one of said branches based upon a filter coefficient assigned by said amplifiers;

the selected branch comprising a series switch and a ground switch configured to feed a signal from the selected branch into an input of an integrator comprising a transconductance amplifier and an integrating capacitor, wherein said transconductance amplifier converts charge of said signal into current and said current is inputted to said integrating capacitor.

21. The system of claim 1, wherein said receive circuit converts the analog samples to decoded digital samples and said decoded digital samples are used to form C-scan images.

22. The system of claim 21, wherein repeated blocks of said receive circuit yield distinct decoded time samples, each decoded time sample being constructed using k received samples, where k is a length of a decoding filter used by said receive circuit, and wherein said k received samples are weighted by filter coefficients of said decoding filter and integrated to yield one of decoded analog sample, wherein said decoded analog samples are digitized to form said decoded digital samples, and wherein said decoded digital samples are apodized and focused to construct C-scan images.

23. The system of claim 1, wherein said receive circuit decodes said received electrical signal after apodizing and delaying samples of said received electrical signal.

24. The system of claim 1, wherein said receive circuit implements an arbitrary, analog, discrete-time filter.

25. The system of claim 1, wherein said pulse generation circuit and said receive circuit are provided on a single integrated circuit.

26. A diagnostic ultrasound system comprising:
a pulse generation circuit configured to provide electrical signals representative of a transmit code sequence;
a transducer configured to receive the electrical signals provided by the pulse generation circuit as pulses using coded excitation according to said transmit code sequence, and to transduce said electrical signals to pulses of energy other than electrical signals; said transducer being further configured to receive echoes of said pulses of energy other than electrical signals and convert the echoes to received electrical signals; and
a receive circuit configured to:
receive said received electrical signals;
perform analog sampling of the received electrical signals;
perform analog decoding of the received electrical signals using information about the coded excitation and using an analog decoder circuit; and
provide a weighted, summed digital signal using information obtained from the analog sampling and the analog decoding;
processing circuit configured to;
receive weighted sum digital signal; and
generate image using the digital signal;
display coupled to processing circuit to display the image.

27. The system of claim 26, wherein said receive circuit weights said analog samples, sums said weighted analog samples and converts a resulting summed, weighted analog signal to a summed, weighted digital signal.

28. The system of claim 26, wherein said diagnostic ultrasound system comprises a medical ultrasonic imaging system.

29. A method of processing a pulse-echo to generate an image, said process comprising:
provide electrical signals representative of a transmit code sequence
receiving an analog electrical signal converted from a received pulse-echo using information about a coded excitation, the pulse-echo elicited in response to the coded excitation;
analog sampling and analog decoding said electrical signal using a receive circuit configured to:
provide analog samples of the analog electrical signal;
provide analog decoding of the samples using an analog decoder circuit including using information about the coded excitation; and
using information obtained from the analog samples and the analog decoding, produce a weighted, summed, digital signal;
generate image using the weighted sum digital signal; and
display the image.

30. The method of claim 29, wherein said processing comprises:
weighing said analog samples to provide weighted, analog samples;
summing said weighted analog samples to provide a summed, weighted, analog signal; and
converting said summed, weighted, analog signal to said summed, weighted, digital signal.

31. The method of claim 29, wherein said processing comprises:
weighting said analog samples to provide weighted, analog samples;
converting said weighted, analog samples to weighted digital samples; and
summing said weighted digital samples to provide said summed, weighted, digital signal.

32. The method of claim 29, wherein said processing comprises:
converting said analog samples to digital samples;
weighting said digital samples to provide weighted, digital samples; and
summing said weighted, digital samples to provide said summed, weighted, digital signal.

33. The method of claim 29, further comprising:
repeating said receiving, said analog sampling, said analog decoding, and said processing to provide a plurality of said summed, weighted digital signals;
apodizing said summed, weighted digital signals; and
focusing said summed, weighted digital signals having been apodized, to construct an image.

34. The method of claim 29, wherein the received analog electrical signal is directed down two circuit paths of a two-level filter, wherein scaled samples are produced by one of said two circuit paths analog multiplying the signals by +1 and the other of the two circuit paths analog multiplying the signals by −1, and, depending upon whether a resulting signal coefficient is +1 or −1, a switch selects one of the circuit paths and passes the scaled sample as a weighted analog sample to a summing device.

35. The method of claim 29, wherein the received analog signal is directed to a differential circuit comprising a switching circuit that implements positive and negative coefficients by interchanging positive and negative terminals of differential branches of said differential circuit; and
wherein said processing comprises summing performed by a differential sampling, switched capacitor integrator with reset capability configured to sample a continuous signal during one phase to provide a sampled signal, and, in a second phase, to add the sampled signal to previous sampled signals.

36. The method of claim 29, further comprising adjusting an adjustable sampling capacitor in regard to a coefficient value configured for weighting said analog signal.

37. The method of claim 29, wherein said weighting is carried out using a switching circuit capable of implementing more than two different filter coefficients by interchanging positive and negative terminals of differential branches of said differential circuit and by providing each differential branch with an adjustable sampling capacitor that is adjustable for multiple different coefficient values.

38. The method of claim 29, wherein said weighting is performed using a plurality of sample and hold circuits, each configured for sampling and holding one sample of the received electrical signal; and said summing is performed by a switched-capacitor integrator configured to commence integration and integrate said samples after all samples from an entire received pulse have been acquired by said sample and hold circuits.

39. The method of claim 29, wherein said weighting is performed using an analog memory bank provided for holding each sample of the received electrical signal over one code length; and wherein said summing is performed using a switched-capacitor integrator configured to commence integration and integrate said samples after all samples from an entire received pulse have been held by said analog memory bank.

40. The method of claim 29, wherein said pulse-echo is an ultrasound pulse-echo.

41. The method of claim 29, wherein said image is a C-scan image.

42. The method of claim 29, wherein repeated blocks of said received analog signals are weighted and summed to yield distinct weighted time samples, each weighted time sample being constructed using k received samples, where k is a length of a decoding filter used during said weighting, and wherein said k received samples are weighted by filter coefficients of said decoding filter and integrated to yield one of said weighted analog samples, wherein said weighted analog samples are digitized to form said weighted digital samples, and wherein said weighted digital samples are apodized and focused to construct C-scan images.

43. The method of claim 29, wherein said weighting comprises taking samples of said electrical signal at selected time intervals to correspond to a delay between reception of said pulse-echo and reception of an aberrant scaled replica of said pulse-echo, so that said pulse-echo and said aberrant scaled replica are scaled and summed by said weighting and summing to effect at least partial cancellation of the aberrant scaled replica.

* * * * *